US009958422B2

(12) United States Patent
Armstrong

(10) Patent No.: US 9,958,422 B2
(45) Date of Patent: *May 1, 2018

(54) METHODS FOR QUANTITATING WATER USING IONIC LIQUID SALTS

(71) Applicant: SIGMA-ALDRICH CO., LLC, St. Louis, MO (US)

(72) Inventor: Daniel W. Armstrong, Arlington, TX (US)

(73) Assignee: Sigma-Aldrich Co. LLC, St. Louis, MO (US)

(*) Notice: Subject to any disclaimer, the term of this patent is extended or adjusted under 35 U.S.C. 154(b) by 0 days. days.

This patent is subject to a terminal disclaimer.

(21) Appl. No.: 14/920,043

(22) Filed: Oct. 22, 2015

(65) Prior Publication Data

US 2016/0041131 A1    Feb. 11, 2016

Related U.S. Application Data

(62) Division of application No. 13/625,659, filed on Sep. 24, 2012, now Pat. No. 9,168,507.

(Continued)

(51) Int. Cl.
| | | |
|---|---|---|
| *G01N 30/00* | (2006.01) |
| *G01N 30/62* | (2006.01) |
| *B01J 20/288* | (2006.01) |
| *B01J 20/29* | (2006.01) |
| *B01J 20/32* | (2006.01) |
| *G01N 1/22* | (2006.01) |

(Continued)

(52) U.S. Cl.
CPC ............ *G01N 30/62* (2013.01); *B01J 20/288* (2013.01); *B01J 20/29* (2013.01); *B01J 20/3204* (2013.01); *B01J 20/3253* (2013.01); *B01J 20/3257* (2013.01); *B01J 20/3282* (2013.01); *B01J 20/3285* (2013.01); *B01J 20/3287* (2013.01); *G01N 1/22* (2013.01); *B01D 53/02* (2013.01); *B01J 2220/84* (2013.01); *B01J 2220/86* (2013.01); *G01N 2030/025* (2013.01); *G01N 2030/8872* (2013.01)

(58) Field of Classification Search
CPC ....................................................... G01N 30/62
USPC ............................................................ 436/39
See application file for complete search history.

(56) References Cited

U.S. PATENT DOCUMENTS

| 8,097,721 B2 | 1/2012 | Armstrong et al. .......... 540/567 |
| 8,182,581 B2 | 5/2012 | Armstrong et al. .............. 95/83 |

OTHER PUBLICATIONS

Tharanga Payagala, Ying Zhang, Eranda Wanigasekara, Ke Huang, Zachary S. Breitbach, Pritesh S. Sharma, Leonard M. Sidisky, and Daniel W. Armstrong "Trigonal Tricationic Ionic Liquids: A Generation of Gas Chromatographic Stationary Phases" Anal. Chem. 2009, 81, 160-173.*

(Continued)

*Primary Examiner* — Christopher Adam Hixson
*Assistant Examiner* — Emily R. Berkeley
(74) *Attorney, Agent, or Firm* — Sigma-Aldrich Co. LLC

(57) ABSTRACT

This disclosure provides methods and devices for quantitating, separating and/or detecting water in a liquid, gas or solid sample comprising one or more chemicals, the method comprising: providing the liquid, gas or solid sample comprising water and the one or more chemicals; and exposing said liquid, gas or solid sample to at least one solid support including at least one dicationic and/or tricationic species of Formula I or II adsorbed, absorbed or immobilized on the solid support.

13 Claims, 10 Drawing Sheets

Related U.S. Application Data

(60) Provisional application No. 61/538,640, filed on Sep. 23, 2011.

(51) Int. Cl.
    *G01N 30/88*     (2006.01)
    *B01D 53/02*     (2006.01)
    *G01N 30/02*     (2006.01)

(56) References Cited

OTHER PUBLICATIONS

Hogan, et al., (1970). "A versatile internal standard technique for the gas chromatographic determination of water in liquids". *Analytical Chemistry.* 42(2):249.

Huang, et al., (2007). "PEG-linked geminal dicationic ionic liquids as selective, highstability gas chromatographic stationary phases". *Anal Bioanal Chem.* 389:2265-2275.

Jayawardhana, et al., (2011). "Rapid, efficient quantification of water in solvents and solvents in water using an ionic liquid-based gc column" *LCGC Europe.* 24(10):516-529.

Office Action (Non-final) dated May 2, 2014 in U.S. Appl. No. 13/625,659.

Office Action (Final) dated Aug. 8, 2014 in U.S. Appl. No. 13/625,659.

\* cited by examiner

1) HAIM-PEG TfO⁻

2) TTP TfO⁻

3) DMIM-PEG TfO⁻

METHODS FOR QUANTITATING WATER USING IONIC LIQUID SALTS

CROSS-REFERENCE TO RELATED APPLICATIONS

This application is a divisional of U.S. non-provisional application No. 13/625,659, filed Sep. 24, 2012, which claims the benefit of U.S. provisional application Ser. No. 61/538,640 filed Sep. 23, 2011. The disclosure of the application is hereby incorporated by reference.

FIELD

The present disclosure relates to methods for separating, detecting and/or quantitating water in a sample and devices therefor. More specifically, the disclosure relates to methods for separating, detecting or quantitating water in various materials using a polyionic liquid salt and devices for water quantitation comprising a polyionic liquid salt.

BACKGROUND

Versatile, rapid and accurate analytical techniques for the detection and quantification of water in a variety of materials remain an important and ubiquitous analytical problem. Indeed water is one of the most prevalent impurities in many industrial and consumer products and processes. In other cases, water is an essential component, the concentration of which must be known accurately and controlled.

The determination of water content in solvents and consumer products, including foods, pharmaceuticals, and industrial materials, is of great importance. Indeed analytical testing for the presence and concentration of water is one of the most frequent, important and ubiquitous measurements made in modern industrial society. Thus a versatile, simple and efficient analytical technique for the accurate quantification of water is imperative. The essentially universal presence of water requires accurate, facile and sensitive techniques to quantify it. While various techniques such as gravimetry, Karl Fisher titration (KFT), gas chromatography, near IR spectrophotometry, solvatochromic sensing, F-NMR spectroscopy, isotope ratio mass spectrometry (IRMS) and others have been reported in the literature, only a few methods are widely accepted and used.

Currently, the most commonly used method for water analysis is the KFT, which was first reported in 1935. In this titrametric method, $I_2$ is reduced to HI in the presence of water. There are four components in the Karl Fischer reagent consisting of: iodine, sulfur dioxide, a suitable base (RN) (originally pyridine was used, but now imidazole is more common); and a suitable solvent such as methanol, ethanol, diethylene glycol monomethyl ether, etc.

The accepted mechanism of this two step reaction is:

$CH_3OH+SO_2+RN \rightarrow [RNH]SO_3CH_3$

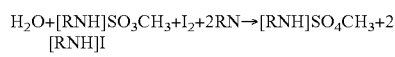

$H_2O+[RNH]SO_3CH_3+I_2+2RN \rightarrow [RNH]SO_4CH_3+2[RNH]I$

The end point is determined potentiometrically. Two types of KFT methods are used. They are the coulometric titration and the volumetric titration. Coulometric titration is used to detect trace amounts of water, ranging from 10 μg to 99 μg (1 ppm-5%), and it requires about 5 g or more of sample. Volumetric titration is used to detect water quantities higher than 1 mg (10 ppm-100%), and the amount of sample required varies from 0.1 mg to 500 mg. Therefore, prior knowledge of the approximate amount of water present in the sample is required in choosing the correct KFT method of analysis.

Although KFT is a well-established method, interference of side reactions, reagent instability, sample insolubility and pH issues prevent it from being accepted as a universal method. Variations on the basic KFT methodologies have been developed in an attempt to overcome these problems. However, many issues still remain, not the least of which is that the reagents degrade with time and there is residual water in all KFT reagents.

Another applied method for water detection is based on gas chromatography (GC). Early attempts using GC were mainly based on packed (molecular sieve) columns, involving both direct detection by thermal conductivity detector (TCD) and indirect detection (i.e. reacting water with calcium carbide to convert to acetylene) with a flame ionization detector (FID). Peak asymmetry, poor sensitivity, poor efficiency, strong adsorption of water and many solvents by the stationary phase, overlapping of the water peak by other larger peaks, and the inability to detect higher amounts of water limited its application in many cases. Attempts to eliminate peak asymmetry, using wide-diameter open tubular columns and capillary columns showed some improvement. Additionally, most conventional capillary column GC stationary phases are degraded by water.

One truly useful, broadly effective capillary GC method for water should meet several criteria including the following: 1) Water should not alter or degrade the stationary phase, thereby altering retention times and peak shapes; 2) There must be a considerable difference in the retention of water and most/all organic solvents especially when the solvent peak is very large relative to the water peak; 3) The water peaks should show good efficiency and symmetry; and 4) The water and solvent chromatogram should have sufficient separation space for an appropriate, baseline separated internal standard.

U.S. Pat. No. 8,182,581 to Armstrong et al reports diionic liquid salts comprising a dicationic or dianionic molecules and a counter-ion, and a method of using such diionic salts for separating one chemical from a mixture of chemicals. The methods comprise steps of providing a mixture of at least one first and at least one second chemical, and exposing that mixture to at least one solid support including a diionic liquid salt.

U.S. Pat. No. 8,097,721 to Armstrong et al describes triionic liquid slats comprising a tricationic or trianionic molecules and a counter-ion, and a method of using such triionic salts for separating one chemical from a mixture of chemicals. The methods comprise steps of providing a mixture of at least one first and at least one second chemical, and exposing that mixture to at least one solid support including a triionic liquid salt.

SUMMARY

This disclosure provides methods for separating, detecting or quantitating water in a liquid, gas or solid sample. In an embodiment, there is provided a method for detecting or quantitating water in a sample comprising: applying a sample to a capillary column having a gas chromatography stationary phase comprising at least one dicationic species of Formula I:

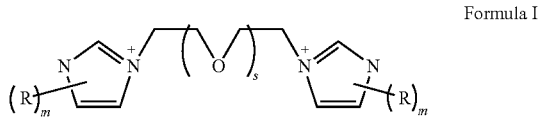

Formula I and a counter-ion, wherein each R is independently selected from the group consisting of alkyl, alkoxy, carbocyclyl, carbocyclylalkyl, heterocyclyl, heterocyclylalkyl and hydroxyalkyl; each m is independently 0, 1, 2, 3 or 4; and s is 1, 2, 3, 4, 5 or 6; and separating water from the sample to detect or quantitate water in the sample.

In another embodiment, there is provided a method for detecting or quantitating water in a sample comprising: applying a sample to a capillary column having a gas chromatography stationary phase comprising at least one tricationic species of Formula II:

Gc(A)$_3$    Formula II and a counter-ion, wherein Gc is phenyl, cycloalkyl, Si, C, N or P, wherein each A is independently selected from the group consisting of:

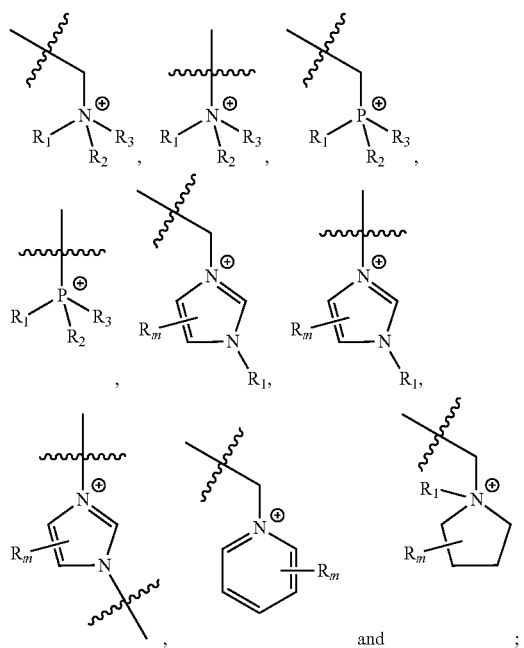

wherein each of $R_1$, $R_2$, $R_3$ and $R_m$ is independently selected from alkyl, alkoxy, carbocyclyl, carbocyclylalkyl, heterocyclyl, heterocyclylalkyl and hydroxyalkyl; and separating water from the sample to detect or quantitate water in the sample.

In yet another embodiment, there is provided a gas chromatography method for detecting or quantitating a component in a sample, comprising: applying a sample to a capillary column having a gas chromatography stationary phase comprising a dicationic species of Formula I or a tricationic species of Formula II and a counter-ion, wherein Formulae I and II are as defined above; separating a component from the sample; and quantitating the component by using a thermal conductivity detector.

In yet another embodiment, there is provided a device for separating, detecting or quantitating water, the device comprising a solid support and at least one polyionic salt comprising a dicationic species of Formula I or a tricationic species of Formula II and a counter-ion, wherein the polyionic salt is adsorbed, absorbed or immobilized on the solid support, wherein Formulae I and II are as defined above.

DETAILED DESCRIPTION

Figure 1:
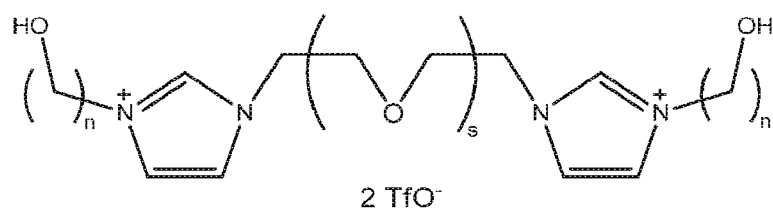
FIG. 1 illustrates ionic liquid gas chromatography stationary phases used in Example 1.
Figure 1:
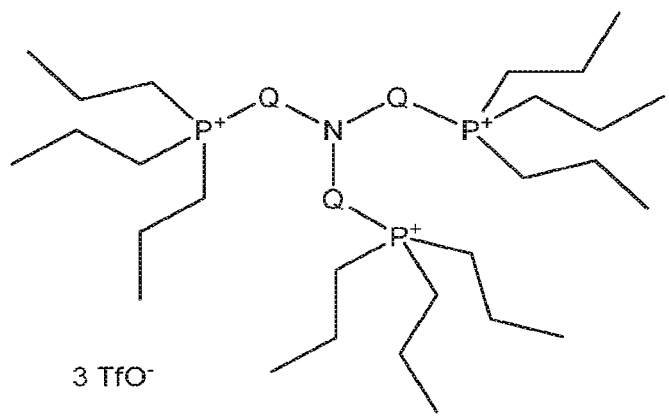
Figure 1:
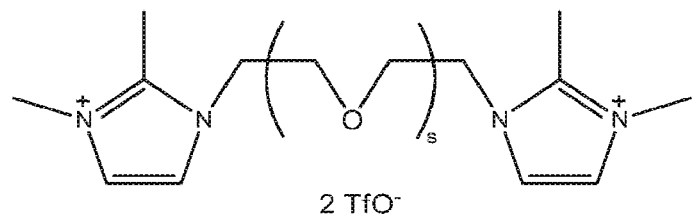

One exemplary embodiment described herein is an effective and sensitive ionic liquid (IL) based capillary gas chromatographic (GC) method with a thermal conductivity detector (TCD) for the determination of water content in samples. The open tubular capillary columns, coated with specific ILs developed in the example below, tremendously increased the sensitivity and ruggedness of this technique. The absolute water content in 50 different solvent samples was determined by using either acetone or acetonitrile as an internal standard. The lower detection limit of this example is about 2 ng water. Samples containing higher levels of water are also readily analyzed without pretreatment. In another exemplar embodiment, organic solvents can be measured in water by the same approach using either TCD or a flame ionization detector (FID). A comparison between IL based columns and commercial columns revealed the enhanced performance of the IL based columns. Standardization was carried out with National Institute of Standards and Technology (NIST) reference materials and the accuracy was compared with another independent method (Karl-Fischer titration). The developed method is highly sensitive, fast, and is not affected by interferences and side reactions common with existing Karl-Fischer-titration (KFT) methods. This exemplar approach can greatly simplify the analysis of water in a variety of applications. The approach can also be applied to gaseous and solid samples.

A. Definitions

The term "alkenyl" refers to a straight or branched hydrocarbyl group with at least one site of unsaturation, i.e. a carbon-carbon, sp2 double bond. In an embodiment, alkenyl has from 2 to 15 carbon atoms. In some embodiments, alkenyl is a $C_2$-$C_{10}$ alkenyl group or a $C_2$-$C_6$ alkenyl group. Examples of alkenyl groups include, but are not limited to, ethylene or vinyl (—CH=$CH_2$), allyl (—$CH_2$CH=$CH_2$), cyclopentenyl (—$O_5H_7$), and 5-hexenyl (—$CH_2CH_2CH_2CH_2$CH=$CH_2$).

The term "alkoxy" refers to an alkylether, i.e., —OR, wherein R is alkyl as defined herein. Non-limiting examples of alkoxy include methoxy (—OCH$_3$), ethoxy, n-propoxy, isopropoxy, n-butoxy, isobutoxy, sec-butoxy, tert-butoxy, and the like.

The term "alkyl" refers to an alkane-derived radical containing from 1 to 20 carbon atoms. Alkyl includes straight chain alkyl, branched alkyl and cycloalkyl. Straight chain or branched alkyl groups contain from 1-15 carbon atoms, such as methyl, ethyl, propyl, isopropyl, butyl, t-butyl, and the like. Alkyl also includes straight chain or branched alkyl groups that contain or are interrupted by one or more cycloalkyl portions. Examples of this include, but are not limited to, 4-(isopropyl)-cyclohexylethyl or 2-methylcyclopropylpentyl. The alkyl group is attached at any available point to produce a stable compound. The term alkyl is also meant to encompass a fully substituted carbon.

The term "alkylene" refers to a divalent alkane-derived radical containing 1 to 20 carbon atoms, such as 1 to 15 carbon atoms, 3 to 20 carbon atoms, 3 to 12 carbon atoms, or 3 to 9 carbon atoms, from which two hydrogen atoms are taken from the same carbon atom or from different carbon atoms. Examples of alkylene include, but are not limited to, methylene —CH$_2$—, ethylene —CH$_2$CH$_2$—, and the like.

The term "alkynyl" refers to a straight or branched carbon-chain group with at least one site of unsaturation, i.e., a carbon-carbon, sp triple bond. In an embodiment, alkynyl is a C$_2$-C$_{15}$ alkynyl group, a C$_2$-C$_{10}$ alkynyl group or a C$_2$-C$_6$ alkynyl group. Non-limiting examples of alkynyl groups include acetylenic (—C≡CH) and propargyl (—CH$_2$C≡CH).

The term "amino" refers to —NH$_2$. The term "amino" is meant to encompass a "monosubstituted amino" wherein one of the hydrogen radicals is replaced by a non-hydrogen substituent; and a "disubstituted amino" wherein both of the hydrogen atoms are replaced by non-hydrogen substituents, which may be identical or different.

The term "ammonium" refers to a positively charged polyatomic cation of the chemical formula

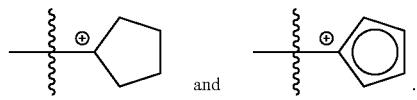

wherein the R groups are individually H or an organic radical group. Ammonium also embraces positively charged or protonated substituted amines (such as protonated tertiary amine). An "optionally substituted ammonium" is an ammonium wherein the organic radical group, R, is optionally substituted with other organic radical groups.

The term "carbocyclyl" means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single ring (monocyclic) or polycyclic ring structure.

A carbocyclyl may be a single ring structure, which typically contains from 3 to 7 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl.

A carbocyclyl may alternatively be polycyclic or contain more than one ring. Examples of polycyclic carbocyclyls include bridged, fused, spirocyclic, and isolated carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, multiple rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl. In an isolated carbocyclyl, the rings are separate and independent, as they do not share any common atoms, but a linker exists between the rings.

The term "carbocyclyl" encompasses protonated carbocyclyl, such as

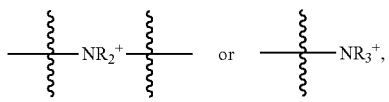

The term "carbocyclylalkyl" refers to the group —Z-carbocyclyl where Z is lower alkylene or substituted lower alkylene group.

The term "diionic salt" is used to describe a salt molecule, although, as the context suggests, it may be used synonymously with "diionic liquid" ("DIL") and "diionic liquid salt" ("DILS"). A "diionic liquid" or "diionic liquid salt" in accordance with the present disclosure is a liquid comprised of diionic salts. Thus, sufficient diionic salt molecules are present such that they exist in liquid form at the temperatures indicated herein. This presumes that a single diionic salt molecule is not a liquid. A diionic liquid is either (1) a dicationic liquid or (2) a dianionic liquid.

A "dicationic liquid salt" or "dicationic liquid", as mentioned above, is either a salt molecule or a liquid comprised of dicationic salt(s), wherein the dicationic salt(s) is formed between a dicationic species and one or more counter-anions of equal and opposite charge. The term is not meant to embrace a single species that has a +2 or −2 charge such as Mg$^{+2}$ or SO$_4^{-2}$. Rather it contemplates a single molecule with two discreet monocationic groups, usually separated by a bridging group. The dicationic liquid of the present disclosure can also be a mixture of one or more dicationic liquid salts as defined herein.

The term "heterocyclyl" means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., N, P, As, O, S and Si), with the remaining ring atoms being independently selected from the group consisting of carbon, oxygen, nitrogen, and sulfur. A heterocyclyl may be a single-ring (monocyclic) or polycyclic ring structure.

The term "heterocyclyl" encompasses protonated heterocyclyls such as pyridinium, pyridazinium, pyrimidinium, pyrazinium, imidazolium, pyrazolium, thiazolium, oxazolium and triazolium.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiadiazolyl, oxadiazolyl (including 1,2,3-oxadiazolyl, 1,2,4-oxadiazolyl, 1,2,5-oxadiazolyl (furazanyl) or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,2,3-dioxazolyly or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, or 1,3,5-oxadiazinyl)), morpholinyl, azepinyl, oxepinyl, thiepinyl, and diazepinyl.

A heterocyclyl may alternatively be polycyclic or contain more than one ring. Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, multiple rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,2-b]-pyridinyl or pyrido[3,4-b]-pyridinyl), and pteridinyl. Other examples of fused-ring heterocyclyls include benzofused heterocyclyls, such as indolyl, isoindolyl (isobenzazolyl, pseudoisoindolyl), indoleninyl (pseudoindalyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,2,3-benzoxazinyl, 1,2,4-benzoxazinyl, or 1,3,4-benzoxazinyl), and benzisoxazinyl (including 1,2-benzisoxazinyl or 1,4-benzisoxazinyl).

The term "heterocyclylalkyl" refers to the group —Z-heterocyclyl where Z is lower alkylene or substituted lower alkylene group.

The term "imidazolium" or "unsubstituted imidazolium" refers to a positively charged polyatomic ion with the chemical structure of

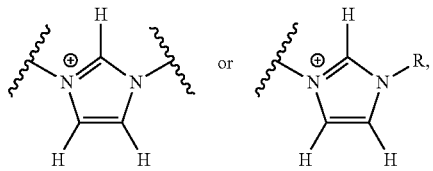

wherein the R group is H or an organic radical group.

The term "protonated tertiary amine" refers to a positively charged polyatomic ion with the chemical formula

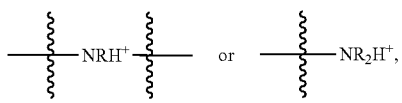

wherein the R groups are organic radical groups. An "optionally substituted protonated tertiary amine" is a tertiary amine wherein the organic radical group, R, is optionally substituted with other organic radical groups.

The term "phosphonium" refers to a positively charged polyatomic ion with the chemical formula

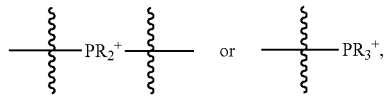

wherein the R groups are individually H or an organic radical group. An "optionally substituted phosphonium" is a phosphonium wherein the organic radical group, R, is optionally substituted with other organic radical groups.

The term "triionic salt" is used to describe a salt molecule, although, as the context suggests, it may be used synonymously with "triionic liquid" ("TIL") and "triionic liquid salt" ("TILS"). A "triionic liquid" or "triionic liquid salt" in accordance with the present disclosure is a liquid comprised of a triionic salt. Thus, sufficient triionic salt molecules are present such that they exist in liquid form at the temperatures indicated herein. A TIL is either (1) a tricationic liquid or (2) a trianionic liquid. A "tricationic liquid salt" or "tricationic liquid", as mentioned above, is either a salt molecule or a liquid comprised of tricationic salt(s), wherein the tri cationic salt(s) is formed between a tricationic species and one or more counter-anions of equal, greater than, or less than opposite charge. This contemplates a single molecule with three discreet monocationic groups, usually separated by bridging groups. The tricationic liquid of the present disclosure can also be a mixture of one or more tricationic liquid salts as defined herein.

The chemical terms defined herein have the same meaning when they are combined with another term(s). For example, the term "alkylamino" means "amino" substituted with "alkyl", each group as defined above.

B. Dicationic Liquid Salts

In one embodiment, there is provided a dicationic liquid salt comprising a dicationic species of Formula I:

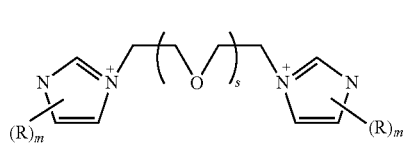

Formula I and at least one counter-anion, wherein each R is one or more substituents independently selected from alkyl, alkoxy, carbocyclyl, carbocyclylalkyl, heterocyclyl, heterocyclylalkyl and hydroxyalkyl; m means a number of R substituents on an imidazolium ring and each m is independently 0 (i.e., no substitution), 1, 2, 3 or 4; and s is 1, 2, 3, 4, 5 or 6.

In a particular aspect, R is one or more independently selected substituents such as methyl, ethyl, propyl, butyl, ethenyl, methoxy, ethoxy, propoxy, butoxy, phenyl, cyclohexane, benzyl, cyclohexanemethyl, hydroxymethyl, hydroxyethyl and hydroxypropyl; m is 0, 1 or 2, particularly 1 or 2; s is 1, 2 or 3, particularly 2 or 3. In some embodiments, m is 1, 2 or 3; and s is 1, 2 or 3.

In another particular aspect, each R is $C_1$-$C_{10}$-alkyl, hydroxyl, carbocyclylalkyl, heterocyclylalkyl or hydroxyalkyl; m is 1 or 2; and s is 2 or 3. In yet another particular aspect, R is methyl, ethyl, propyl, butyl, hydroxyalkyl or benzyl; m is 1 or 2, particularly 1; and s is 2 or 3.

In a further embodiment, a dicationic liquid salt comprises a dicationic species corresponding in structure to Formula I(a):

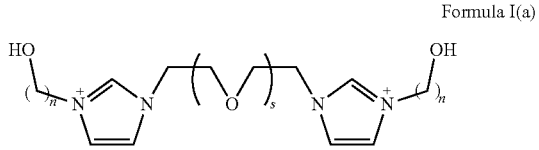

Formula I(a)

and at least one counter-anion, wherein n is independently 1, 2, 3, 4, 5, 6, 7, 8, 9 or 10; and s is 1, 2, 3, 4, 5 or 6. In a particular aspect, n is independently 1, 2 or 3; and s is 1, 2 or 3, particularly 2 or 3.

In a particular embodiment, n is 1; s is 3; and the counter ion is triflate:

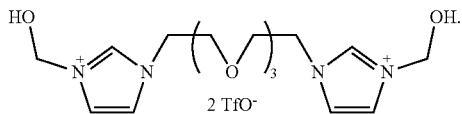

In a particular embodiment, n is 2 and in a further embodiment, n is 2, s is 3, and the counter ion is fluoride or triflate, and thus, the diionic species is:

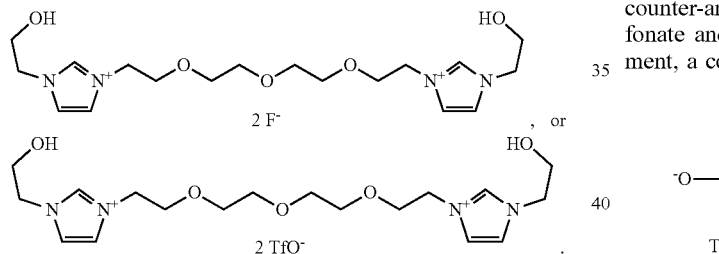

In a further embodiment, a dicationic liquid salt comprises a dicationic species corresponding in structure to Formula I(b):

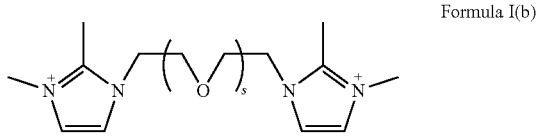

Formula I(b)

and at least one counter-anion, wherein s is 1, 2, 3, 4, 5 or 6, particularly 1, 2 or 3, and more particularly 2 or 3.

In a particular embodiment, s is 3 and the counter ion is triflate, and the diionic species is:

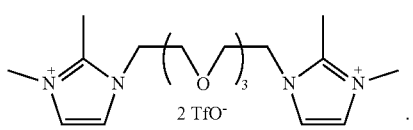

In a further embodiment, a dicationic liquid salt comprises a dicationic species of Formula I(c):

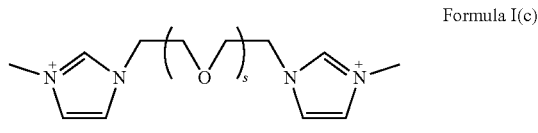

Formula I(c)

and at least one counter-anion, wherein s is 1, 2, 3, 4, 5 or 6, particularly 1, 2 or 3, and more particularly 2 or 3.

In a particular embodiment, s is 3 and the counter ion is triflate, and the diionic species is:

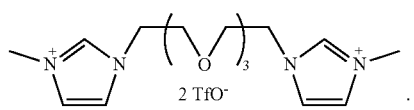

Figure 7:
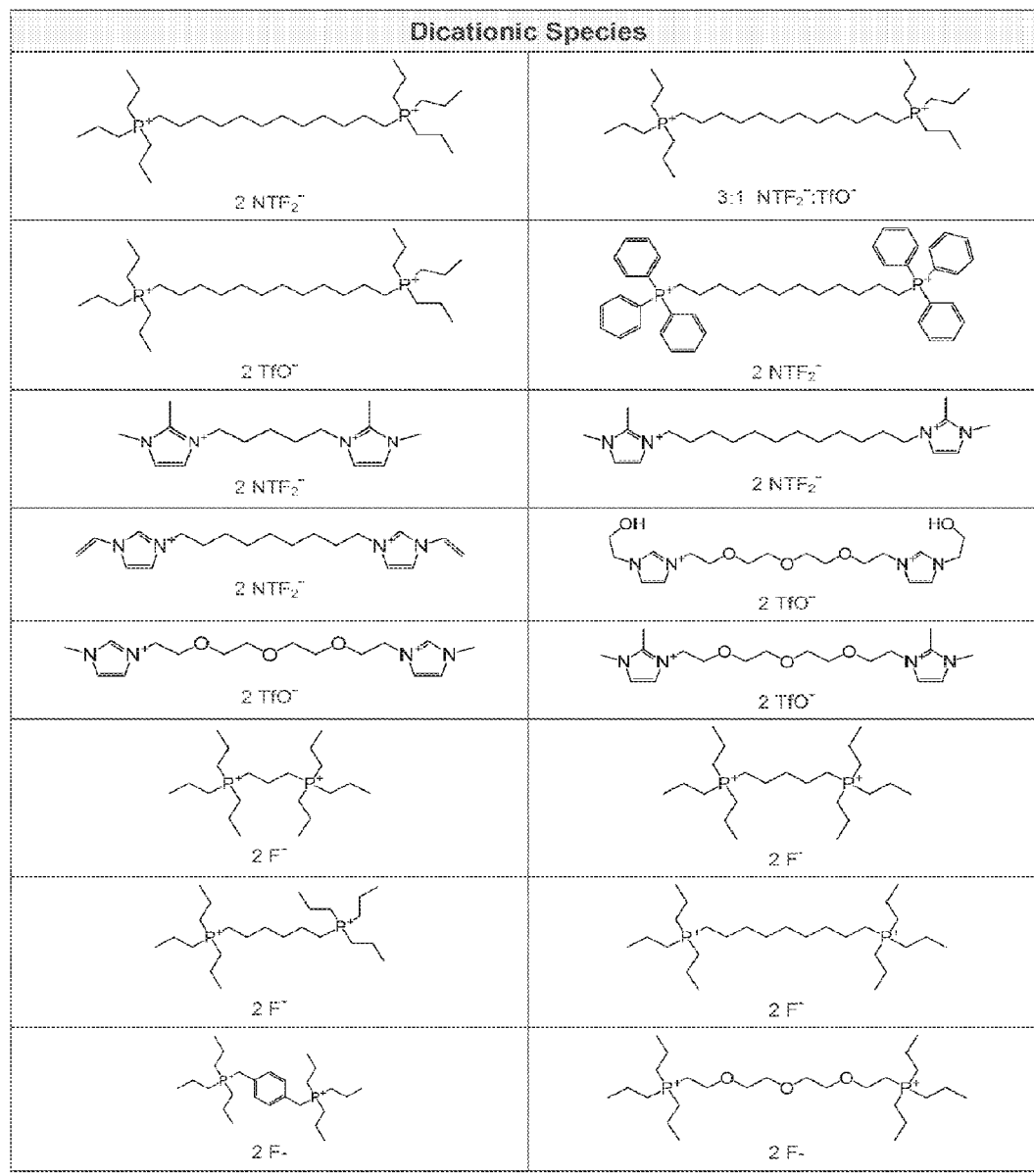
FIG. 7 is a table of exemplary dicationic species.
Figure 7:
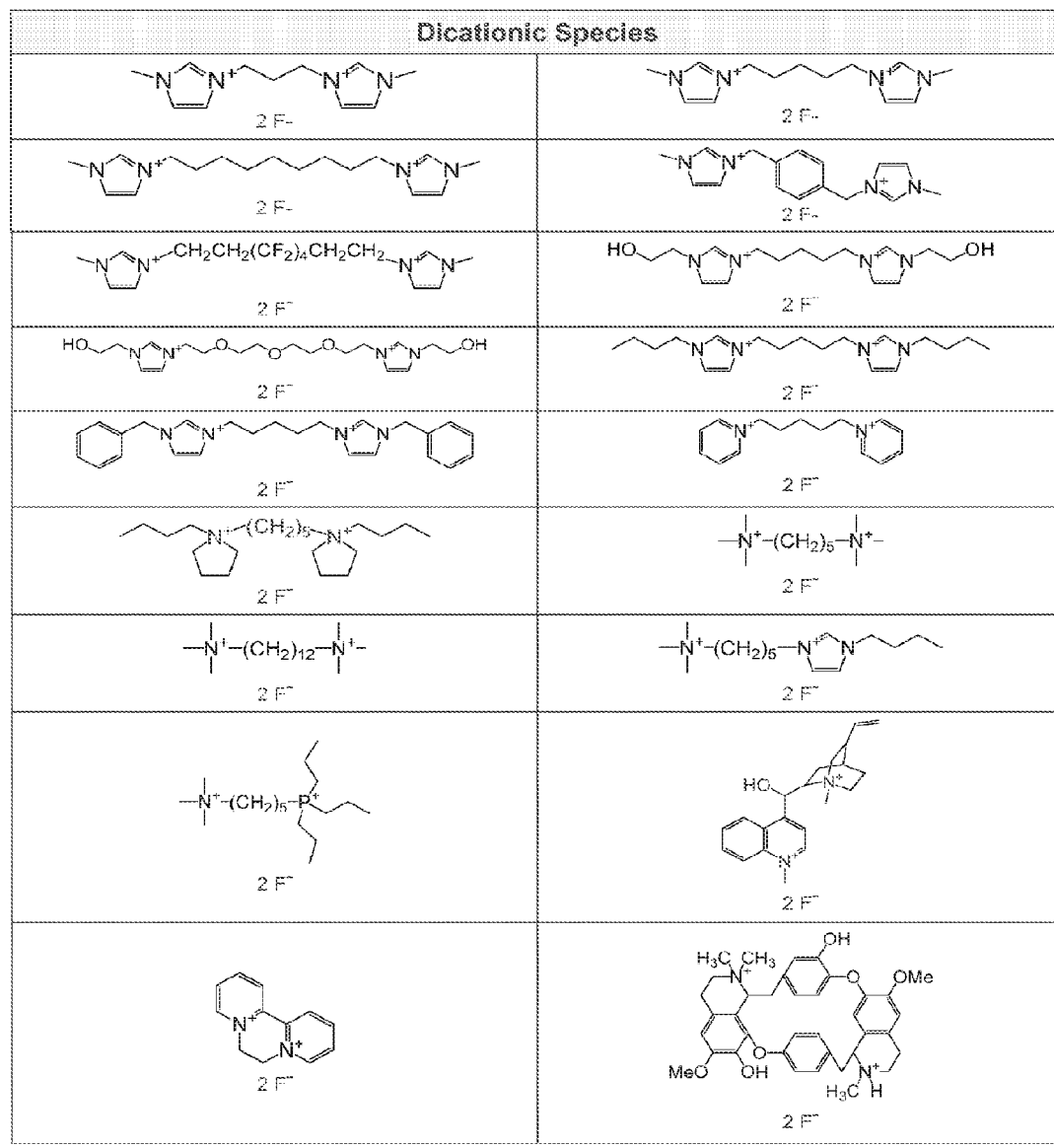

FIGS. 1 and 7 and Table 1 describe exemplary embodiments of additional dicationic species.

In general, the counter-anions used to create the dicationic liquid salt may be any suitable counter-anions. The salt forming counter-anions may be monoionic such as, for example, $Br^-$, or dianionic such as, for example, succinic acid. The counter-anions need not be identical. Examples of suitable counter-anions include, without limitation, $OH^-$, $F^-$, $Br^-$, $Cl^-$, dicarboxylate, disulfonate, disulfate, triflate ($TfO^-$), $NTf_2^-$, $PF_6^-$ and $BF_4^-$. In a particular aspect, a counter-anion is selected from triflate, $NTf_2^-$, haloalkylsulfonate and halocarboxylate. In another particular embodiment, a counter-anion is triflate, as shown below:

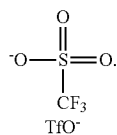

$TfO^-$

In one embodiment, the dicationic liquid salt has a solid/liquid transformation temperature at about 100° C. or lower, will not substantially decompose and is substantially nonvolatile at a temperature below 200° C. and has a liquid range of about 200° C. or higher. In another embodiment, the present disclosure comprises a dicationic liquid salt having a temperature of solid/liquid transformation temperature at 25° C. or lower, which will not substantially decompose and is substantially nonvolatile at a temperature below 300° C. or has a liquid range of about 300° C. or higher.

In one embodiment, either the dicationic species is chiral, having at least one stereogenic center. In such instances, the dicationic liquid salts may be racemic (or in the case of diastereomers, each pair of enantiomers is present in equal amounts) or they may be optically enhanced. "Optically enhanced" in the case of enantiomers means that one enantiomer is present in an amount which is greater than the other. In the case of diastereomers, at least one pair of enantiomers is present in a ratio of other than 1:1. Indeed, the dicationic liquid salts may be "substantially optically pure" in which one enantiomer or, if more than one stereogenic center is present, at least one of the pairs of enantiomers, is present in an amount of at least about 90% relative to the other enantiomer. The diionic liquid salts of the disclosure may also be optically pure, i.e., at least about 98% of one enantiomer relative to the other.

C. Tricationic Liquid Salts

In some embodiments, there is provided a central group tricationic liquid salt comprising a trication of Formula II:

$$Gc(A)_3 \qquad \text{Formula II}$$

wherein Gc is a central group and each A is independently a monoionic group; and at least one counter-anion, wherein each A may be the same or different so long as they are all cations.

In some embodiments, A is chiral and therefore contains at least one stereogenic center. Non-limiting examples of A include carbocyclyl, heterocyclyl, quaternary ammonium, protonated tertiary amine, phosphonium or arsonium groups.

In some embodiments, each A is a monoionic group selected from the group consisting of alkylene, alkenylene, alkynylene, (—$CH_2$-carbocyclyl-$CH_2$—)$_v$, and polysiloxyl; wherein alkylene, alkenylene, and alkynylene optionally contain one or more heteroatoms selected from the group consisting of O, N, S and Si; wherein the monoionic group is substituted with a cationic group selected from the group consisting of heterocyclyl, quaternary ammonium, protonated tertiary amine and phosphonium; wherein the cationic group optionally is substituted with one or more substituents independently selected from the group consisting of alkyl, cycloalkyl, phenyl, halo, alkoxy and hydroxyl; wherein the alkyl optionally is substituted with one or more substituents selected from the group consisting of hydroxy and phenyl; and v is selected from the group consisting of 1 to 20, inclusive.

In some embodiments, the A groups are identical.

In some embodiments, the monoionic A group selected from the group consisting of imidazolium, ammonium, phosphonium and pyridinium. In some embodiments, A is independently selected from the group consisting of:

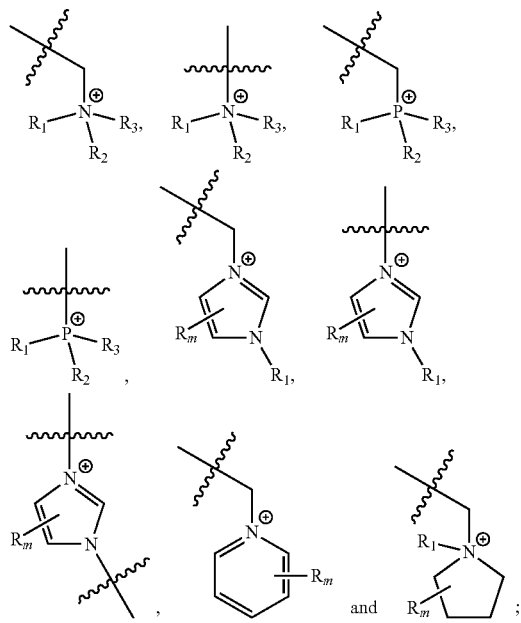

wherein $R_1$, $R_2$, $R_3$ and $R_m$ can be the same or different, and each of $R_1$, $R_2$, $R_3$ and $R_m$ is independently selected from alkyl, alkoxy, carbocyclyl, carbocyclylalkyl, heterocyclyl, heterocyclylalkyl and hydroxyalkyl. In a particular aspect, each of $R_1$, $R_2$, $R_3$ and $R_m$ is independently selected from methyl, ethyl, propyl, butyl, ethenyl, methoxy, ethoxy, propoxy, butoxy, phenyl, cyclohexane, benzyl, cyclohexanemethyl, hydroxymethyl, hydroxyethyl and hydroxypropyl.

Gc is a central group (also referred to as a center or central moiety) that may be substituted or unsubstituted, saturated or unsaturated, aliphatic, including straight or branched chains, cyclic or aromatic, and which may contain, in addition to, or even instead, of carbon atoms and hydrogen, N, P, As, O, S and Si atoms. The central group is not a charged ionic group. In some particular aspects, Gc is phenyl, cycloalkyl, Si, C, N or P; and A is as described above.

The central group (Gc in Formula II) or center interposed among the ionic species can be of any length or any composition which affords a polyionic liquid salt of suitable properties. These include the groups identified as Gc above. There are certain factors that should be considered in selecting such a central moiety. First, the larger the polyionic molecule in general, the greater the chance that the melting point or temperature of solid/liquid transformation will be elevated. This may be less of a concern where the liquid range need not be extensive and/or where the temperature of solid/liquid transformation need not be very low. If, however, as is often the case, one desires a liquid range of about 200° C. or higher and/or a solid/liquid transformation temperature at 100° C. or lower, the size of the overall molecule can become a larger and larger factor. On the other hand, a larger mass might be good for certain mass spectrometry applications. Second, in some embodiments, it is preferable that the central group have some flexibility. In such embodiments, a linear molecule, usually saturated, or a cyclic or polycyclic group of limited unsaturation can be used as the central group. In some other embodiments, a more rigid polyionic molecule may be desirable. In such embodiments, a high degree of unsaturated groups, very rigid and/or sterically bulky groups, such as those found in, for example, cholesterol, and polyunsaturated aliphatic groups with extensive unsaturation, acryl groups, and cyclic groups including multiple fused ring structures, can be used as the center group. In still another embodiment, the central group can be a single atom such as C, Si, N and P.

The central group may be aliphatic, cyclic, or aromatic, or a mixture thereof. It may contain saturated or unsaturated carbon atoms or a mixture of same with, for example, alkoxy groups (ethoxy, propoxy, isopropoxy, butoxy, and the like). It may also include or be made completely from alkoxy groups, glycerides, glycerols and glycols. The central group may contain hetero-atoms such as O, N, S or Si and derivatives such as siloxanes, non-protonated tertiary amines and the like. The central group may be made from one or more cyclic or aromatic groups such as a cyclohexane, an immidazole, a benzene, a diphenol, a toluene, or a xylene group or from more complex ring-containing groups such as a bisphenol or a benzidine. These are merely representative and are not meant to be limiting. Generally, however, the central group will not contain an ionically charged species, other than the polyanions or polycations. And, it is possible to make mixtures of PILS each having, for example, the same cationic species, and each having the same counterions, but differing in the central groups alone. Other variations are also contemplated.

In some embodiments, this disclosure provides a polyionic liquid salt in which the central group is a linear central group having lengths ranging from a length equivalent to that of a saturated aliphatic carbon chain of between about 2 and about 40 carbon atoms (e.g., n=$C_2$-$C_{40}$ when central group is composed of carbon). Such a polyionic liquid salt is termed a linear-Gc-based polyionic liquid salt. More preferably, the length should be approximately that resulting from a saturated aliphatic carbon chain of about 3 to about 30 carbon atoms in length.

In some other embodiments, the disclosure provides a polyionic liquid salt in which the central group is a cyclic central group having at least a three member ring. Such a polyionic liquid salt is termed a cyclic-Gc-based polyionic liquid salt. In embodiments involving a cyclic central group, the number of carbons and/or any heteroatoms in the central group can be between 3 and about 40 (e.g., n=$C_3$-$C_{40}$ when central group is composed of carbon). More preferably, the number of carbons and/or any heteroatoms in the central group can be between 5 to about 30. The cyclic central group can have, but are not limited to a 3, 4, 5, 6 or 7-membered ring. The cyclic central group can also have a fused multiple ring.

The cyclic central group can be an alicyclic group containing one or more all-carbon rings which may be either saturated or unsaturated, either substituted or unsubstituted. Exemplary alicyclic groups include, but are not limited to, cycloalkanes such as cyclopropane, cyclobutane, cyclohexane and cycloheptane, bicyclic alkanes such as norbornene and norbornadiene, and polycyclic cycloalkane such as Decalin, Spiro groups, which have bicyclic connected through one carbon atom, and cycloalkenes such as cyclobutene, cyclopropene and cyclohexene.

The cyclic central group can be an aromatic group containing one or more all-carbon rings which may be either substituted or unsubstituted. Exemplary aromatic groups include, but are not limited to, benzene, naphthalene, anthracene, benzo[a]pyrene, benzo[ghi]pyrene, chrysene, coronene, fluoranthene, tetracene, pentacene, phenanthrene, pyrene and triphenylene.

The cyclic central group can be a heterocyclic group that contains atoms in addition to carbon, such as sulfur, oxygen or nitrogen, as part of the ring. The heterocyclic groups can be either saturated or unsaturated, either substituted or unsubstituted, either aromatic or non-aromatic, single or fused. The heterocyclic groups can have, for example, 3, 4, 5, 6 or 7 membered rings.

The cyclic groups can also have fused multiple rings. Examples of fused multiple rings include, but are not limited to, benzocyclobutene, pentalene, benzofuran, isobenzofuran, indole, isoindole, benzothiophene, benzo[c]thiophene, benzimidazole, purine, indazole, benzoxazole, benzisoxazole, benzothiazole, naphthalene, anthracene, quinoline, isoquinoline, quinoxaline, acridine, quinazoline and cinnoline.

In embodiments in which the central group comprises a linear group and a cyclic group, the monoionic groups can be distributed across the central group in any manner. For example, some of the monoionic groups, A, are conjugated to the cyclic portion while other monoionic groups are conjugated to the linear portion of the central group.

Gc can be optionally substituted with one or more Rc substituents independently selected from the group consisting of a proton, substituted or unsubstituted, saturated or unsaturated, straight or branched aliphatic chain (such as alkyl), cyclic group (such as cycloalkyl), aromatic group (such of phenyl or substituted phenyl), halo, alkoxy and hydroxyl.

In one embodiment, a polyionic liquid salt is a compound having the following formula:

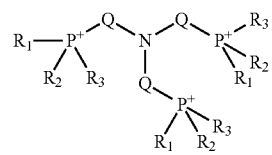

wherein each of $R_1$, $R_2$ and $R_3$ is independently methyl, ethyl, propyl, butyl, hydroxyalkyl or benzyl; and each Q is independently selected from the group consisting of alkylene, alkenylene, alkynylene, (—$CH_2$-carbocyclyl-$CH_2$—)$_n$, and polysiloxyl; wherein alkylene, alkenylene, and alkynylene optionally contain one or more heteroatoms selected from the group consisting of O, N, S and Si; wherein Q is optionally substituted with one or more substituents selected from the group consisting of alkyl, alkenyl, alkynyl, and alkoxy; and n is selected from the group consisting of 1 to 20, inclusive.

In a further embodiment, $R_1$, $R_2$ and $R_3$ are propyl, and the tricationic liquid salt comprises a tricationic species of Formula II(a):

Formula II(a)

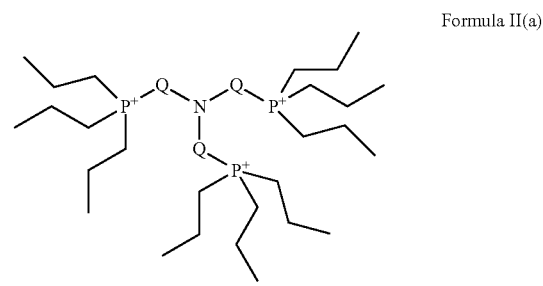

and at least one counter-anion such as, for example, trifluoromethylsulfonate, 3TfO$^-$. In a particular embodiment, the variable Q is $C_{1-10}$-alkylene, particularly $C_{1-6}$-alkylene, and more particularly $C_{1-3}$-alkylene.

In a particular embodiment, Q is ethylene and the counter ion is triflate, and the triionic species is:

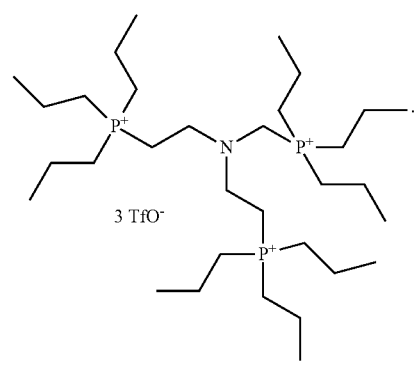 [SMILES: CCC[P+](CCC)(CCC)CCN(CC[P+](CCC)(CCC)CCC)C[P+](CCC)(CCC)CCC]

In some embodiments, a compound has a structure of Formula II(b):

Formula II(b)

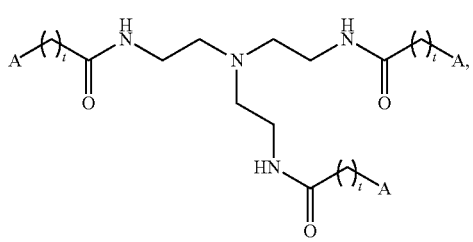

wherein each t is independently selected from the group consisting of 1 to 20, inclusive; and each A is independently as defined previously.

In one embodiment, A is phosphonium; and each of $R_1$, $R_2$ and $R_3$ is independently methyl, ethyl, propyl, butyl, hydroxyalkyl or benzyl.

In a further embodiment, A is phosphonium, $R_1$, $R_2$ and $R_3$ are propyl, t is 5, and the anion is triflate, and the triionic species is:

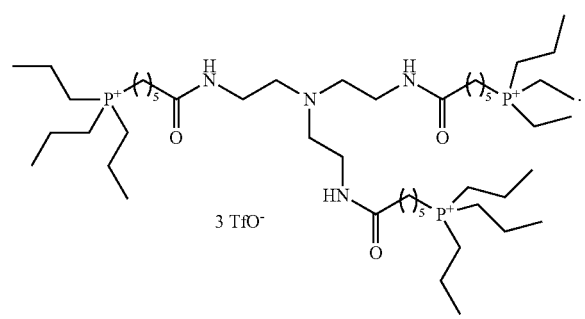

In another embodiment, A is phosphonium, $R_1$, $R_2$ and $R_3$ are propyl, t is 5, and the anion is $NTF_2^-$ or $F^-$, and the triionic species is:

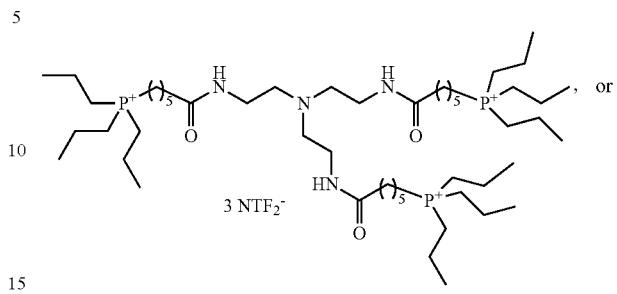

, or

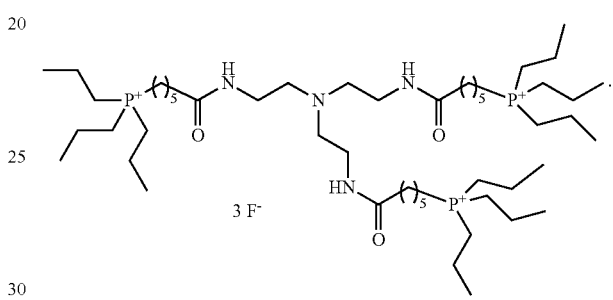

In another embodiment, A is imidazolium. In a further embodiment, $R_1$ is methyl or hydroxymethyl, t is 5, and the imidazolium has optionally one or more methyl substitution, and the anion is $F^-$. Non-limiting examples of such triionic species include:

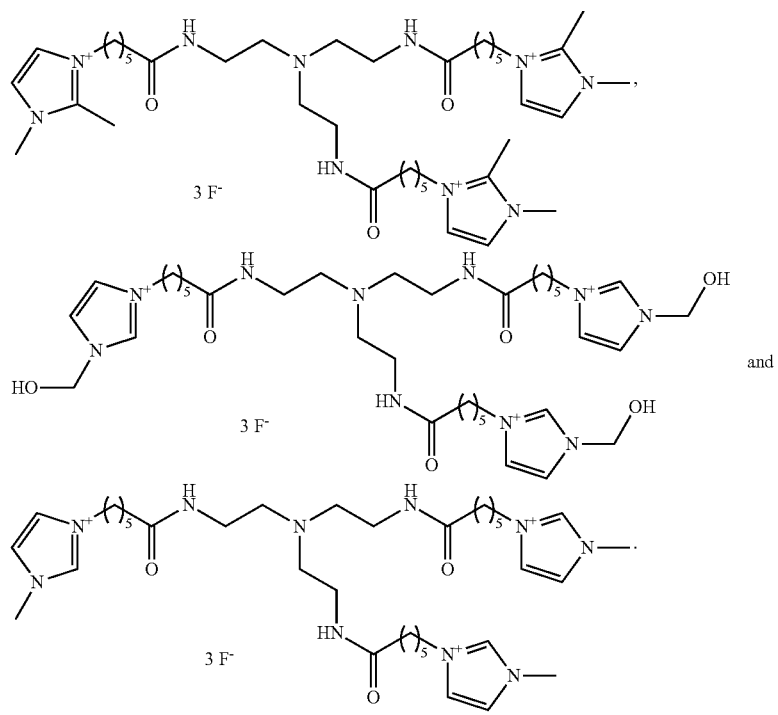

Figure 8:
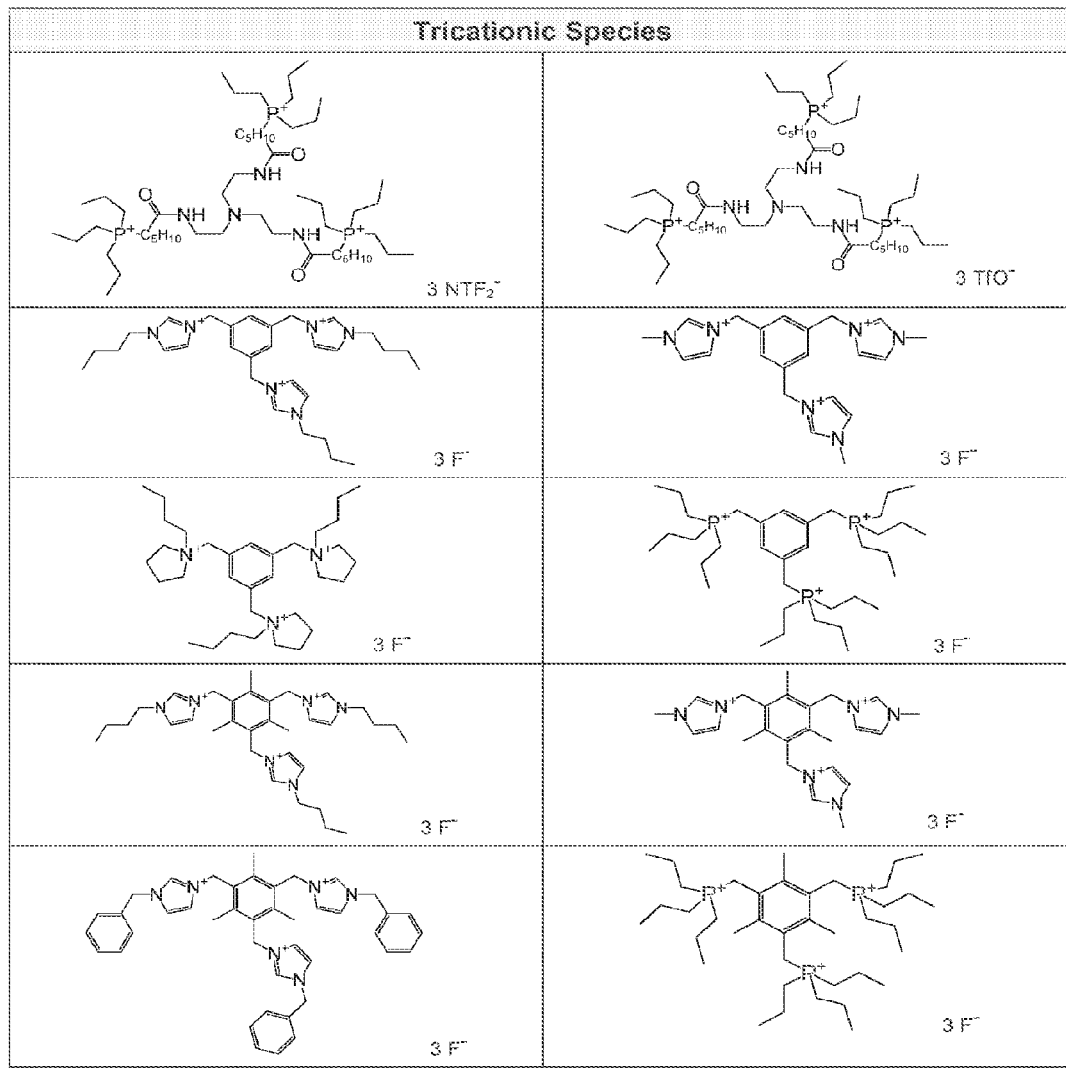
FIG. 8 is a table of exemplary tricationic species.
Figure 8:
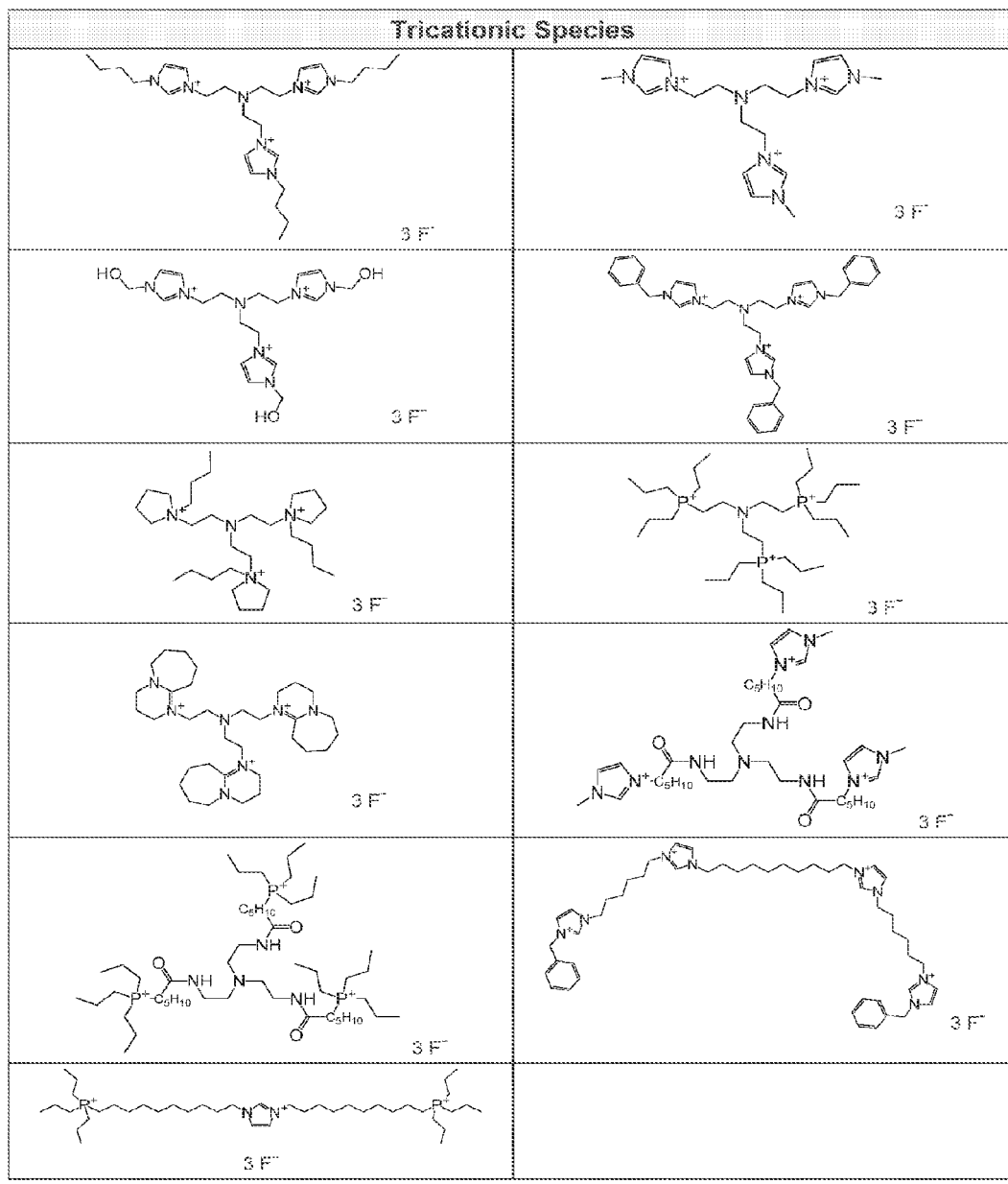

FIGS. 1 and 8 and Table 1 describe exemplary embodiments of additional tricationic species.

In general, the counter-anions used to create the tricationic liquid salt may be any suitable counter-anions. The salt forming counter-anions may be monoionic such as, for example only, Br⁻, or trianionic, such as, again for example only, succinic acid. The counter-anions need not be identical. Examples of suitable counter-anions include, without limitation, $OH^-$, $F^-$, $Br^-$, $Cl^-$, dicarboxylate, disulfonate, disulfate, triflate ($TfO^-$), $NTf_2^-$, $PF_6^-$ and $BF_4^-$ may be used. In a particular aspect, triflate, $NTf_2^-$, haloalkylsulfonate and halocarboxylate is used.

In one embodiment, the tricationic liquid salt has a solid/liquid transformation temperature at about 100° C. or lower, will not substantially decompose and is substantially nonvolatile at a temperature below 200° C. and has a liquid range of about 200° C. or higher. In another embodiment, the present disclosure comprises a tricationic liquid salt having a temperature of solid/liquid transformation temperature at 25° C. or lower, which will not substantially decompose and is substantially nonvolatile at a temperature below 300° C. or has a liquid range of about 300° C. or higher.

In one embodiment, either the tricationic species is chiral, having at least one stereogenic center. In such instances, the tricationic liquid salts may be racemic (or in the case of diastereomers, each pair of enantiomers is present in equal amounts) or they may be optically enhanced. "Optically enhanced" in the case of enantiomers means that one enantiomer is present in an amount which is greater than the other. In the case of diastereomers, at least one pair of enantiomers is present in a ratio of other than 1:1. Indeed, the tricationic liquid salts may be "substantially optically pure" in which one enantiomer or, if more than one stereogenic center is present, at least one of the pairs of enantiomers, is present in an amount of at least about 90% relative to the other enantiomer. The triionic liquid salts of the disclosure may also be optically pure, i.e., at least about 98% of one enantiomer relative to the other.

D. Devices

There is also provided a device useful in chemical separation, detection or quantitation comprising: a solid support and at least one dicationic species of Formula I or tricationic species of Formula II which is adsorbed, absorbed or immobilized on the solid support. Any dicationic or tricationic species described herein, such as the dicationic and/or tricationic compounds shown in FIGS. 1, 7 and 8, may be suitable for use in chemical separation. Such a device is particularly useful for chemical separation, detection or quantitation of water from liquid, gas or solid samples.

In a particular aspect, the device comprises a syringe, a hollow needle, a plunger, and the solid support being attached to the syringe. In a particular aspect, the device comprises an open tubular capillary column coated with an ILS stationary phase.

Another embodiment is a device useful in chemical separation, detection or quantitation, especially of water content, comprising: a solid support and one or more ILSs, such as for example species of FIG. 1, which is adsorbed, absorbed or immobilized on the solid support.

In a particular embodiment, the device for quantitating water in a liquid, gas or solid sample comprises a solid support and at least one polyionic salt comprising a dicationic species of Formula I or a tricationic species of Formula II and a counter-ion, wherein the polyionic salt is adsorbed, absorbed or immobilized on the solid support:

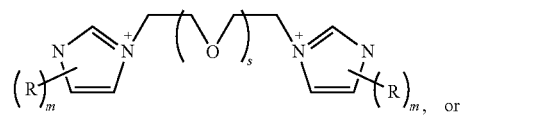

Gc(A)₃, wherein each R is independently selected from the group consisting of alkyl, alkoxy, carbocyclyl, carbocyclylalkyl, heterocyclyl, heterocyclylalkyl and hydroxyalkyl; each m is independently 0, 1, 2, 3 or 4; and s is 1, 2, 3, 4, 5 or 6, wherein Gc is phenyl, cycloalkyl, Si, C, N or P, wherein each A is independently selected from the group consisting of:

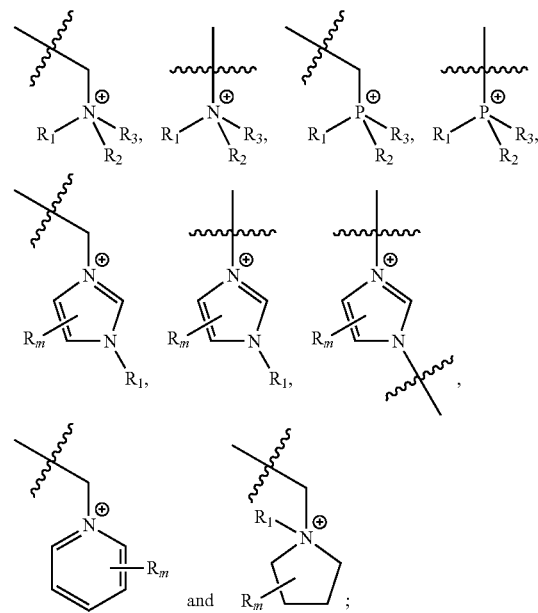

wherein each of $R_1$, $R_2$, $R_3$ and $R_m$ is independently selected from alkyl, alkoxy, carbocyclyl, carbocyclylalkyl, heterocyclyl, heterocyclylalkyl and hydroxyalkyl.

E. Stationary Phases and Polymerization

There is provided an immobilized dicationic liquid salt including one or more dicationic liquid salts (with or without monoionic materials) as stationary phases, particularly in GC. These stationary phases are highly selective, highly stable, and highly resistant to temperature degradation. These materials can be non-cross-linked (which often means that they are absorbed or adsorbed on a solid support or column), can be "partially" cross-linked or "more highly" cross-linked (which often means that they are "immobilized" on a solid support or column) and can be composed of a mixture of dicationic liquid salts and dicationic material and/or monocationic materials or can be made completely of dicationic liquid salts in accordance with the present disclosure. The presence of unsaturated groups facilitates cross-linking and/or immobilization.

In the case of non-cross-linked stationary phases, the polycationic liquid salts used may be saturated, unsaturated or a mixture of both. It should be understood, however, particularly if some amount of unsaturated polycationic liquid salt(s) is used, and especially where heat is used to fix the stationary phase, or the stationary phase is heated during use, as in gas chromatography, some degree of cross-linking is possible.

"Partially" cross-linked stationary phases in accordance with the present disclosure permit production of a more stable, highly selective stationary phase, allowing for high efficiency separations at temperatures up to approximately 280'C.

"More highly" cross-linked stationary phases in accordance with the present disclosure can provide superior efficiency and stability even at temperatures up to 350'C and higher. In "more highly cross-linked" stationary phases, the amount of polyionic species will surpass that of any monoionic species. Preferably, more highly cross-linked stationary phases will be composed substantially exclusively (90% or more) of immobilized polyionic liquid salts in accordance with the disclosure.

In a particular embodiment, the stationary phases are made from a polyionic species which is chiral and optically enhanced. Moreover, cross-linking and/or immobilization of the polyionic liquid salt in a column as a stationary phase, or to a solid support for SPE, SPME, TS-SPME, SPME/MALDI, ion chromatography, ion exchange chromatography, headspace analysis or other analytical or separation technique, does not appear to affect the selectivity of the stationary phase, thereby preserving its dual nature retention behavior.

And while stationary phases for GC and, in particular, capillary GC are one particular aspect of the present disclosure, the polyionic liquid salts can be used as a stationary phase in other forms of chromatography including, for example, LC and HPLC. Not only are the methods of creating stationary phases, solid supports and/or columns containing same contemplated, the stationary phases, solid supports and columns themselves and the use of columns and solid supports containing these stationary phases in chromatography, and other analytical or separation techniques are contemplated as specific aspects of the disclosure.

A polyionic liquid salt can be coated on a capillary (or solid support) and optionally, subsequently polymerized and/or cross-linked by, for example, two general methods. In the first method, the polyionic liquid salt is coated via the static coating method at 40° C. using coating solution concentrations ranging from 0.15-0.45% (w/w) using solutions of methylene chloride, acetone, ethyl acetate, pentane, chloroform, methanol, or mixtures thereof. After coating of the polyionic liquid salt is complete, the column is purged with helium and baked up to 100° C. The efficiency of naphthalene (other molecules such as n-hydrocarbons or Grob Test Mixture can also be used for this purpose) is then evaluated to examine the coating efficiency of the monomer ionic liquid stationary phase. If efficiency is deemed sufficient, the column is then flushed with vapors of azo-tert-butane, a free radical initiator, at room temperature. After flushing with the vapors, the column is then fused at both ends and heated in an oven using a temperature gradient up to 200° C. for 5 hours. The column is gradually cooled and then re-opened at both ends, and purged with helium gas. After purging with helium gas overnight, the column is then heated and conditioned up to 200° C. After conditioning, the column efficiency is then examined using naphthalene at 100° C. and the stationary phase coated layer examined under a microscope. Note that the cross-linking process can, and often does, also cause immobilization. "Immobilized" in the context of the disclosure means covalently or ionically bound to a support or to another ionic liquid (including diionic liquid salts) or both. This is to be compared with ionic liquids which may be absorbed or adsorbed on a solid support. Solid supports in these particular instances are intended to include columns (e.g., the walls of the columns).

It is not necessary, however, to cross-link these materials prior to their use in GC. They may be adsorbed or absorbed in a column, or indeed on any solid support. However, at higher temperatures, their viscosity may decrease and they can, in some instances, flow and collect as droplets which can change the characteristics of the column. Immobilization or partial cross-linking also reduces the vapor pressure of the stationary phase film which translates into lower column bleed thereby increasing the useful upper temperature limit of the phase and column.

In another embodiment, there is provided a process which includes the free radical reaction of ionic liquid monomers to provide a more durable and robust stationary phase, as well as the cross-linked and/or immobilized stationary phases and the columns that include same. By partially cross-linking the ionic liquid stationary phase using a small percentage of free radical initiator, high efficiency capillary columns are produced that are able to endure high temperatures with little column bleed. It was found that low to moderate temperature separations (30° C.-280° C.) can be carried out with high selectivity and efficiency using special partially cross-linked ionic liquid stationary phase mixtures. These stationary phases retain their "gelatinous," "semi liquid," amorphous state. For separations conducted at higher temperatures (300° C.-400° C.), more highly cross-linked/immobilized stationary phases are well-suited to provide high selectivity and efficient separations with low column bleed. The effect of different functionalized ionic liquid salt mixtures and initiator concentrations is studied for these two types of stationary phases. The goal is to maximize their separation efficiency, thermal stability, and column lifetime, without sacrificing the unique selectivity of the stationary phase.

The following materials can be used to prepare cross-linked stationary phases comprising diionic liquid salts in accordance with the present disclosure: 1-vinylimidazole, 1-bromohexane, 1-bromononane, 1-bromododecane, 1,9-dibromononane, 1,12-dibromododecane, 1-bromo-6-chlorohexane, 1-methylimidazole, N-Lithiotrifluoromethanesulfonimide, AIBN, dichloromethane and ethyl acetate.

It has been demonstrated previously that room temperature ionic liquids act as broadly applicable, superb gas chromatographic stationary phases in that they exhibit a dual nature retention behavior. Consequently, ionic liquid stationary phases have been shown to separate, with high efficiency, both polar and nonpolar molecules on a single column. By producing stationary phases that are either partially or highly cross-linked, it is of interest to ensure that the solvation thermodynamics and solvation interactions inherent to ionic liquids are still retained by their immobilized analogues.

In another embodiment a mixed stationary phase (MSP) is provided. The MSP comprises at least one dicationic liquid salt of the disclosure and stationary phase material such as, but not limited to, polysiloxanes, polyethylene glycols ("PEGs"), methylpolysiloxanes, phenyl substituted methylpolysiloxane, nitrile substituted methylpolysiloxane and carbowax. Such MSPs can be used as a stationary phase in chromatography such as GC, LC and HPLC as well as in SPE and SPME. The MSPs can be non-cross-linked (e.g., absorbed or adsorbed on a solid support or column), can be "partially" cross-linked or "more highly" cross-linked (i.e., immobilized on a solid support or column). The dicationic liquid salt may also be cross-linked or otherwise reacted with the stationary phase material or merely mixed therewith.

Appropriate combinations of the polycationic liquid salt and the stationary phase material for producing a MSP is based on the particular application as are the proportions of the dicationic liquid salt and the stationary phase material in the MSP.

In a particular embodiment, the ratio of the polycationic liquid salt and the stationary phase material in the MSP is from about 1:9 (i.e., about 10% of polycationic liquid salt and 90% of stationary phase material) to about 9:1 (i.e., about 90% of polycationic liquid salt and about 10% of stationary phase material), about 1:3 (i.e., about 25% of polycationic liquid salt and about 75% of stationary phase material) to about 3:1 (i.e., about 75% of polycationic liquid salt and about 25% of stationary phase material), about 1:2 (i.e., about 33% of polycationic liquid salt and about 67% of stationary phase material) to about 2:1 (i.e., about 67% of polycationic liquid salt and about 33% of stationary phase material), or about 1:1 (i.e., about 50% of polycationic liquid salt and about 50% of stationary phase material) (w/w). Chromatography employing MSP may perform better, e.g., having higher selectivity, than chromatography employing polycationic liquid salt or the stationary phase alone. As an example, an MSP comprising a simple mixture of about 67% (dibutyl imidazolium)$_2$(CH$_2$)$_9$ and about 33% of methylpolysiloxane with about 5% phenyl substitution was prepared and used to coat a column. This MSP was shown to exhibit better separation of an essential oil. A cross-linked version of the MSP can also be used.

In addition, the disclosure also provides methods of preparing MSPs, solid supports and/or columns containing same, the MSPs, solid supports, syringes, tubes, pipettes tips, needles, vials, and columns themselves, and the use of columns and solid supports containing such MSPs in chromatography and other analytical or separation techniques such as those described elsewhere herein.

F. Methods of Quantitating, Separating and/or Detecting Water

Analyzing water in organic solvents is generally damaging for traditional commercial columns, leading to appreciable degradation and continuously changing chromatograms. It is found that a stationary phase using polyionic liquid salts is not substantially altered or degraded by water. Therefore, this disclosure provides improved methods for quantitating, separating and/or detecting water in a liquid, gas or solid sample comprising one or more chemicals, the method comprising: providing the liquid, gas or solid sample comprising water and the one or more chemicals; and exposing said liquid, gas or solid sample to at least one solid support including at least one dicationic and/or tricationic species, such as a species of Formula I or II, which is adsorbed, absorbed or immobilized on the solid support.

Water contents in products, such as pharmaceutical or food products, can have influence on their physicochemical properties. In particular cases, water contents have to be strictly controlled to comply with industry/government regulations and guidance, such as regulations of the Food and Drug Administration (FDA). Thus, a method for quantitating, separating and/or detecting water of this disclosure has broad application in many industries. In various embodiments, the method of this disclosure is performed in chemical, pharmaceutical and/or food industry for various purposes. Non-limiting examples of such applications include detection/quantitation of water in solvents, determination of water purity, and detection/quantitation of water in food products or alcoholic beverages.

In an embodiment, the method is used to quantitate water in a liquid sample such as organic solvents. Non-limiting examples of such organic solvents include acetic acid, acetone, acetonitrile, anisole, benzene, 1-butanol, 2-butanol, 2-butanone, t-butyl alcohol, carbon tetrachloride, chlorobenzene, 1-chlorobutane, chloroform, 2-chloropropane, cyclohexane, cyclohexanone, 1,2-dichlorobenzene, 1,2-dichloroethane, 1,3-dichloropropane, diethyl ether, di(ethylene glycol) ethyl ether, 1,2-dimethoxy-ethane (glyme, DME), dimethyl-formamide (DMF), dimethyl sulfoxide (DMSO), dioxane, ethanol, ethyl acetate, ethylene glycol, heptane, hexane, methanol, methyl t-butyl ether (MTBE), methylene chloride, N-methyl-2-pyrrolidinone (NMP), nitrobenzene, nitromethane, nitroethane, octane, 1-octanol, pentane, petroleum ether (ligroine), 1-propanol, 2-propanol, pyridine, tetrahydrofuran (THF), toluene, triethyl amine, o-xylene, m-xylene, and p-xylene.

In a particular embodiment, a method for quantitating, separating and/or detecting water comprises use of a capillary gas chromatographic method employing a solid support including at least one dicationic and/or tricationic species of Formula I or II. A method for quantitating, separating and/or detecting water may comprise direct detection using a thermal conductivity detector (TCD).

In an embodiment, a method of this disclosure further comprises producing a chromatogram showing one or more peaks of molecules contained in the sample. A water and solvent chromatogram produced by the method has sufficient separation space for an appropriate, baseline separated internal standard. The chromatogram shows a considerable difference in the retention of water and all organic solvents. In various embodiments, water peak of the chromatogram shows good efficiency and symmetry.

Any dicationic and/or tricationic species described herein, such as the species shown in FIGS. 1, 7 and 8, may be used for quantitating, separating and/or detecting water in a sample. In various aspects, the dicationic and/or tricationic species is selected from species of Formulae I(a), I(b), I(c), II(a) and II(b). In a particular aspect, the dicationic and/or tricationic species is selected from species of FIG. 1. In a more particular aspect, the method uses a solid support containing a polyionic liquid salts comprising a species selected from the group consisting of:

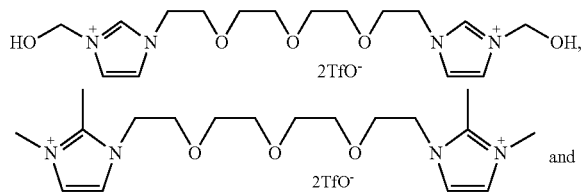

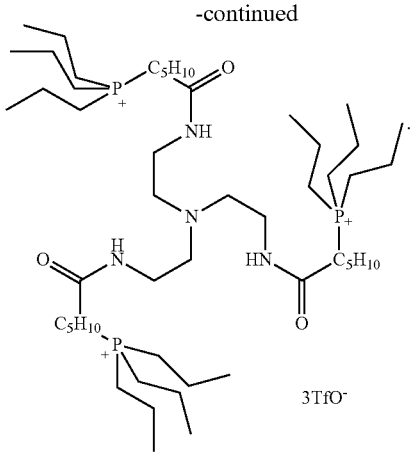

3TfO⁻

"Retaining" in this context does not mean permanently. Separation can occur in a syringe device by removal of the device from the sample or ejection of the second chemical. In the case of a chromatography column, the first chemical (or water) will be absorbed or adsorbed at a different rate than the second chemical, which may be at a greater rate or a lower rate, thus resulting in separation. Both are moved through the column by a mobile phase, which can be a liquid or a gas (e.g., helium) and their interaction with the stationary phase (the ionic liquid materials on the solid support) at different rates causes separation. This is what is meant by "retention" in the context of chromatography. However, in certain types of chromatography, it is also possible that the first chemical is bound to the stationary phase while the second chemical is not and is carried through the column by the mobile phase until it elutes. The first chemical can be eluted or removed separately and this is also embraced by the word "retained."

In a particular embodiment, there is provided a liquid, gas or solid chromatography method for detecting or quantitating a component in a liquid, gas or solid sample, comprising: applying a sample to a capillary column having a gas chromatography stationary phase comprising a dicationic species of Formula I or a tricationic species of Formula II and a counter-ion, wherein Formulae I and II are as defined above; separating a component from the sample; and quantitating the component by using a detector. In various embodiments, the component to be quantitated by the method is water impurity or organic solvent impurity in the liquid sample.

EXAMPLES

The following examples are merely illustrative, and do not limit this disclosure in any way.

Example 1

An ionic liquid (IL) based capillary gas chromatographic method with TCD for the direct determination of water content in liquid samples was examined. The unique nature of ILs, including; high thermal stabilities, variable polarities and exceptional stability to water and oxygen make them excellent choices as stationary phases for this methodology. As shown below, open tubular capillary columns, coated with specific IL stationary phases (developed for water analysis) can tremendously enhance the sensitivity, applicability and reliability of this technique. Furthermore, analysis times can be decreased to 6 minutes or even less than 3 minutes in many cases, and samples with virtually any concentration of water can be analyzed. The efficacy of this approach is demonstrated with 50 different solvent samples.

1.1. Apparatus

The analysis was performed using an Agilent Technologies 6890N gas chromatograph (Agilent technologies Inc., Wilmington, Del.), equipped with a 7683B series autoinjector, TCD and Chemstation plus software (Rev. B.01.03). An Agilent technologies 10 μl syringe (5181-1267), was used with the autosampler, while a Hamilton 10 μl syringe was used for all manual injections. The other experimental parameters are given in Tables 1 and 2 below. The fused silica capillary columns were coated with IL stationary phases synthesized as previously reported. The columns were 30 m long, 0.25 mm internal diameter (I.D.) and 0.2 μm film thickness. KF analysis was performed using Aquastar V1B volumetric titrator (EM Science, a division of EM industries, Inc., Cherry Hill, N.J.).

TABLE 1

GC/TCD parameter for the analysis of water.

| Carrier gas | Helium |
|---|---|
| Carrier gas flow rate (ml/min) | 1.0 |
| Inlet temperature (° C.) | 250 |
| Detector temperature (° C.) | 250 |
| Injection volume (μl) | Vary (0.2-5) |
| Oven temperature (° C.) | Vary (40-120) |
| Analysis mode | Splitless |

TABLE 2

Experimental parameters for detection of water in 50 solvents.

| | HMIM-PEG | | | TTP | | | DMIM-PEG | | |
|---|---|---|---|---|---|---|---|---|---|
| Sample | Oven Temp (° C.) | IS | Inj. Vol. (μl) | Oven Temp (° C.) | IS | Inj. Vol. (μl) | Oven Temp (° C.) | IS | Inj. Vol. (μl) |
| Acetic acid | 120 | A | 0.2 | 120 | A | 2.0 | 100 | C | 0.2 |
| Acetone | 70 | C | 2.0 | 70 | C | 1.0 | 70 | C | 1.0 |
| Acetonitrile | 50 | A | 0.2 | 70 | A | 0.2 | 70 | A | 2.0 |
| Anisole | X | X | X | 120 | A | 1.0 | 70 | C | 2.0 |
| Benzene | 50 | C | 5.0 | 70 | C | 5.0 | 70 | C | 5.0 |
| 1-Butanol | 50 | C | 0.2 | 70 | C | 1.0 | X | X | X |
| 2-Butanol | 50 | C | 0.2 | X | X | X | 70 | A | 0.2 |
| 2-Butanone | 70 | C | 2.0 | 70 | C | 1.0 | 70 | C | 0.2 |
| t-Butyl alcohol | 40 | C | 0.2 | 70 | A | 0.2 | 70 | C | 0.2 |
| Carbon tetrachloride | 70 | C | 5.0 | 70 | C | 5.0 | 70 | C | 5.0 |

TABLE 2-continued

Experimental parameters for detection of water in 50 solvents.

| | HMIM-PEG | | | TTP | | | DMIM-PEG | | |
|---|---|---|---|---|---|---|---|---|---|
| Sample | Oven Temp (° C.) | IS | Inj. Vol. (μl) | Oven Temp (° C.) | IS | Inj. Vol. (μl) | Oven Temp (° C.) | IS | Inj. Vol. (μl) |
| Chlorobenzene | 50 | A | 1.0 | 70 | C | 1.0 | 70 | A | 1.0 |
| 1-Chlorobutane | 70 | C | 3.0 | 70 | C | 5.0 | 70 | C | 5.0 |
| Chloroform | 50 | C | 1.0 | 70 | A | 5.0 | 70 | C | 5.0 |
| 2-Chloropropane | 50 | C | 1.0 | 70 | C | 2.0 | 70 | C | 2.0 |
| Cyclohexane | 70 | C | 5.0 | 70 | C | 5.0 | 70 | C | 5.0 |
| Cyclohexanone | 70 | A | 1.0 | 120 | A | 2.0 | 100 | C | 0.2 |
| 1,2-Dichlorobenzene | X | X | X | 100 | A | 2.0 | X | X | X |
| 1,2-Dichloroethane | 50 | C | 2.0 | 70 | A | 2.0 | 70 | C | 0.2 |
| 1,3-Dichloropropane | 50 | A | 0.2 | X | X | X | 50 | A | 2.0 |
| Diethyl ether | 70 | C | 2.0 | 70 | C | 2.0 | 70 | C | 2.0 |
| Di (ethylene glycol) ethyl ether | 120 | A | 1.0 | 120 | A | 0.5 | 100 | C | 0.2 |
| 1,2-Dimethoxy-ethane (glyme, DME) | 70 | C | 2.0 | 70 | C | 2.0 | 70 | C | 0.2 |
| Dimethyl-formamide (DMF) | 100 | A | 1.0 | 120 | A | 0.2 | 100 | C | 0.2 |
| Dimethyl sulfoxide (DMSO) | 120 | A | 1.0 | 120 | A | 0.2 | 100 | C | 0.2 |
| Dioxane | 50 | A | 0.2 | 70 | A | 1.0 | 50 | A | 0.2 |
| Ethanol | 50 | A | 0.2 | 70 | A | 0.2 | 50 | A | 0.2 |
| Ethyl acetate | 50 | C | 1.0 | 70 | C | 2.0 | 70 | C | 5.0 |
| Ethylene glycol | 120 | A | 0.2 | 120 | A | 0.2 | 100 | C | 0.2 |
| Heptane | 70 | C | 5.0 | 70 | C | 5.0 | 70 | C | 5.0 |
| Hexane | 70 | C | 5.0 | 70 | C | 5.0 | 70 | C | 5.0 |
| Methanol | 50 | A | 0.2 | 70 | A | 0.2 | 70 | A | 0.2 |
| Methyl t-butyl ether (MTBE) | 70 | C | 2.0 | 70 | C | 1.0 | 70 | C | 0.2 |
| Methylene chloride | 70 | C | 2.0 | 70 | C | 2.0 | 70 | C | 2.0 |
| N-methyl-2-pyrrolidinone (NMP) | 120 | A | 0.2 | 120 | A | 0.5 | 100 | A | 0.2 |
| Nitrobenzene | 120 | A | 2.0 | 120 | A | 2.0 | 100 | A | 1.0 |
| Nitromethane | 50 | A | 0.2 | X | X | X | X | X | X |
| Nitroethane | 50 | A | 0.2 | X | X | X | X | X | X |
| Octane | 50 | C | 5.0 | 70 | C | 5.0 | 70 | C | 5.0 |
| 1-Octanol | 70 | C | 1.0 | 120 | A | 2.0 | 100 | C | 5.0 |
| Pentane | 70 | C | 5.0 | 70 | C | 5.0 | 70 | C | 5.0 |
| Petroleum ether (ligroine) | 70 | C | 5.0 | 70 | C | 3.0 | 70 | C | 5.0 |
| 1-Propanol | 50 | A | 0.2 | X | X | X | 70 | A | 0.2 |
| 2-Propanol | 50 | A | 0.2 | 70 | A | 2.0 | 70 | C | 0.2 |
| Pyridine | X | X | X | 70 | A | 2.0 | X | X | X |
| Tetrahydrofuran (THF) | 70 | C | 2.0 | 70 | C | 1.0 | 70 | C | 0.2 |
| Toluene | 40 | C | 1.0 | 50 | A | 2.0 | 70 | C | 5.0 |
| Triethyl amine | 50 | C | 2.0 | 70 | C | 2.0 | 70 | C | 2.0 |
| o-Xylene | 50 | A | 1.0 | X | X | X | 50 | A | 3.0 |
| m-Xylene | 50 | A | 1.0 | X | X | X | 50 | A | 5.0 |
| p-Xylene | 50 | A | 1.0 | X | X | X | 50 | A | 5.0 |

IS is the abbreviation for "internal standard" which was either A = acetone or C = acetonitrile.

1.2. Materials

The water reference material: 8509, moisture in methanol (MeOH, 97±13 ppm water) was obtained from National Institute of Standards and Technology (NIST, Gaithersburg, Md.). The 4 Å molecular sieves, hydranal water standard 1.0, tetrahydrofuran (THF) and both the internal standards (IS), acetone and acetonitrile, were purchased from Sigma-Aldrich (St. Louis, Mo.). Aquastar combititrant 2 and Aquastar methanol were purchased from EMD chemicals (Gibbstowm, N.J.). The high purity water was obtained by filtering the deionized water with Millipore, synergy 185. The testing solvents were from, Sigma-Aldrich, Mallinckrodt, EMD, Fisher, Omni solvent, and Acros organics.

1.3. Sample Preparation

The accurate quantification of water was achieved using one of two internal standards (ISs), either acetone or acetonitrile. Two different ISs were available in case one co-eluted with the analyte solvent under the conditions of the experiment. Internal standards were dried to <10 mg/kg by storing over 30% w/v 3 A molecular sieves for seven days prior to use. A typical sample preparation involved drying a 2 ml autosampler vial overnight at 130° C. followed by the addition of approximately 1 ml of solvent. The mass of the solvent was recorded using an analytical balance. 5.0 mg of internal standard was added prior to analysis.

1.4. Methods

For initial screening, the columns were conditioned at 120° C. for 2 hours and high purity water was injected, 0.1 μl, using 100:1 split ratio at the desired temperature. The sample of interest was injected in the splitless mode (0.2 μl to 5 μl), in order to examine the separation between water and the bulk solvent. This preliminary experiment helped in determining which IS should be used.

Water quantitation was achieved by integration of the internal standard peak and the water peak. The concentration of internal standard in mg/kg was multiplied by the ratio of water peak to internal standard peak and the result was divided by the response factor. The resulting number represents the concentration of water in the sample in mg/kg. Each solvent was prepared in triplicate and each individual sample was injected in triplicate for a total of n=9 individual integrations for each solvent analyzed.

1.5. Detection Limit and Quantitation Limit

The detection limit (LOD) and the quantitation limit (LOQ) were calculated according to the guidelines of the US Food and Drug Administration (FDA), using the following equations:

$$LOD = \frac{3.3\sigma}{S}$$

$$LOQ = \frac{10\sigma}{S}$$

wherein σ is the standard deviation of the response, and S is the slope of the calibration plot.

The σ is normally obtained from the standard deviation of the blank sample. Since it is impossible to obtain a sample without water, the first point of the calibration plot, where there is no added water, is used as the blank sample and its standard deviation was used as σ. The slope was obtained from the regression analysis of the plot; peak area ratio of water and I.S. vs amount of water.

1.6. Results

FIG. 1 shows the structures of the three ionic liquids that were used as stationary phases in this example, i.e., (1) bis-3-hydroxyalkylimidazolium-PEG triflate (HMIM-PEG TfO$^-$); (2) trigonal tripropylphosphonium triflate (TTP TfO$^-$); and (3) bis-2,3-dimethylimidazolium-PEG triflate (DMIM-PEG TfO$^-$). Generally, IL stationary phases containing trifluoromethylsulfonate (TfO$^-$) anions resulted in more symmetric water peak shapes than those of that contained $PF_6^-$, $BF_4^-$ or bis[(trifluoromethyl)sulfonyl]imide ($NTf_2^-$), with the same cation. The triflate counterion is important in delivering sharp, symmetrical water peak shapes. In addition to the IL-based GC columns, a commercially available polyethylene glycol (PEG) column also was evaluated for comparison purposes.

Figure 2:
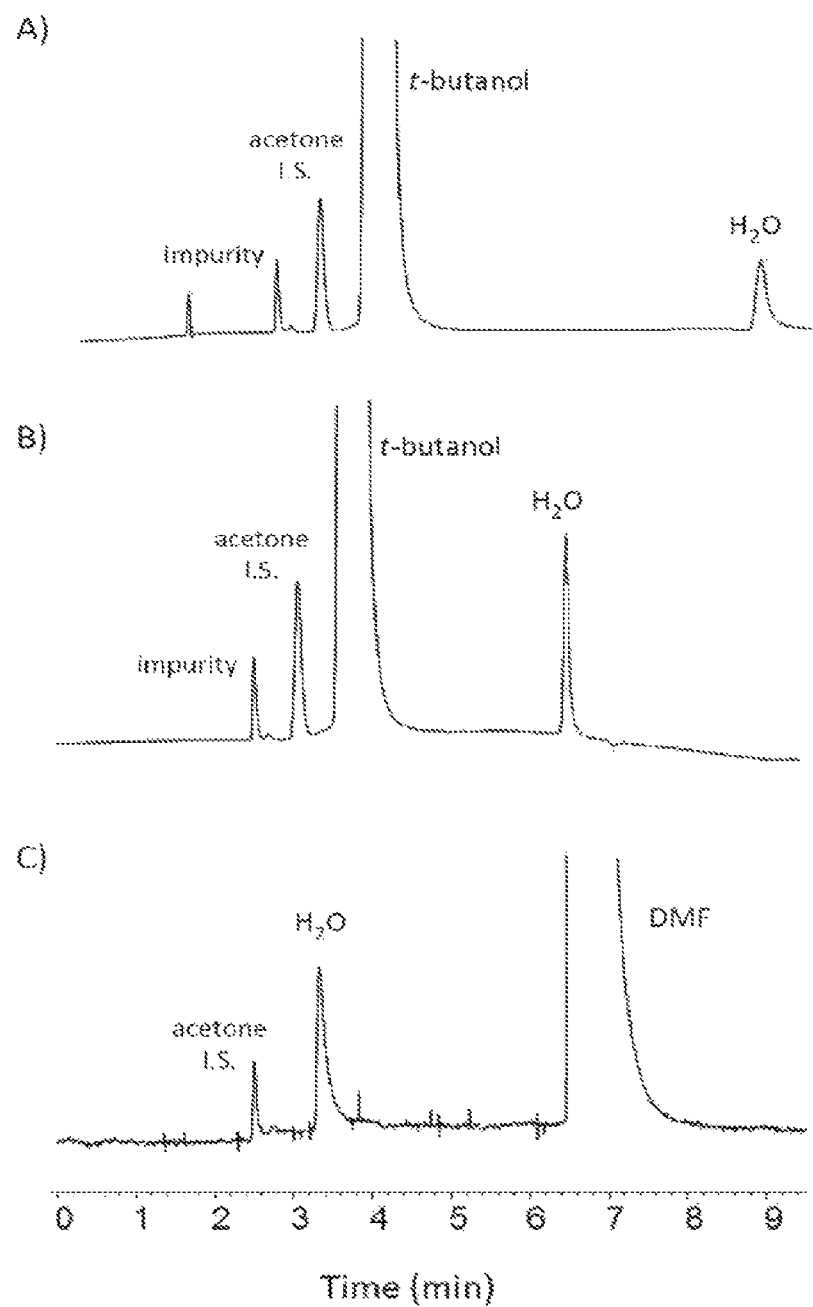
FIG. 2 is a series of chromatograms illustrating the relative retention orders of water and different organic solvents.

FIG. 2 shows the gas chromatography separations of small amounts of water impurities from two of the organic solvents that were analyzed. Chromatograms A and C are isothermal separations. Chromatogram B is for the same sample as in A. However a temperature gradient was used to decrease the analysis time and further "sharpen" the water peak. This enhanced the sensitivity and precision of the method. Conditions for chromatogram A were: 1 µl injection; 50° C.; analysis time: 9 minutes; Internal Standard: acetone (0.4%). Conditions for chromatogram B were: 1 µl injection; 50° C. (hold 2 minutes), ramp 10 dpm to 80° C.; analysis time: 6 minutes, Internal Standard: acetone (0.4%). Conditions for chromatogram C were: 0.2 µl injection; 110° C., analysis time: 8 minutes, Internal Standard: acetone (0.2%). The water peak can be eluted either before or after the large organic solvent peak depending on the relative elution order of the two on the ionic liquid-based stationary phases. In most cases the "separation window" between the water and solvent peaks is sufficiently large as shown in FIG. 2(A) that a thermal gradient can be used to further narrow the peak width of water and reduce analysis times as shown in FIG. 2(B).

Figure 3:
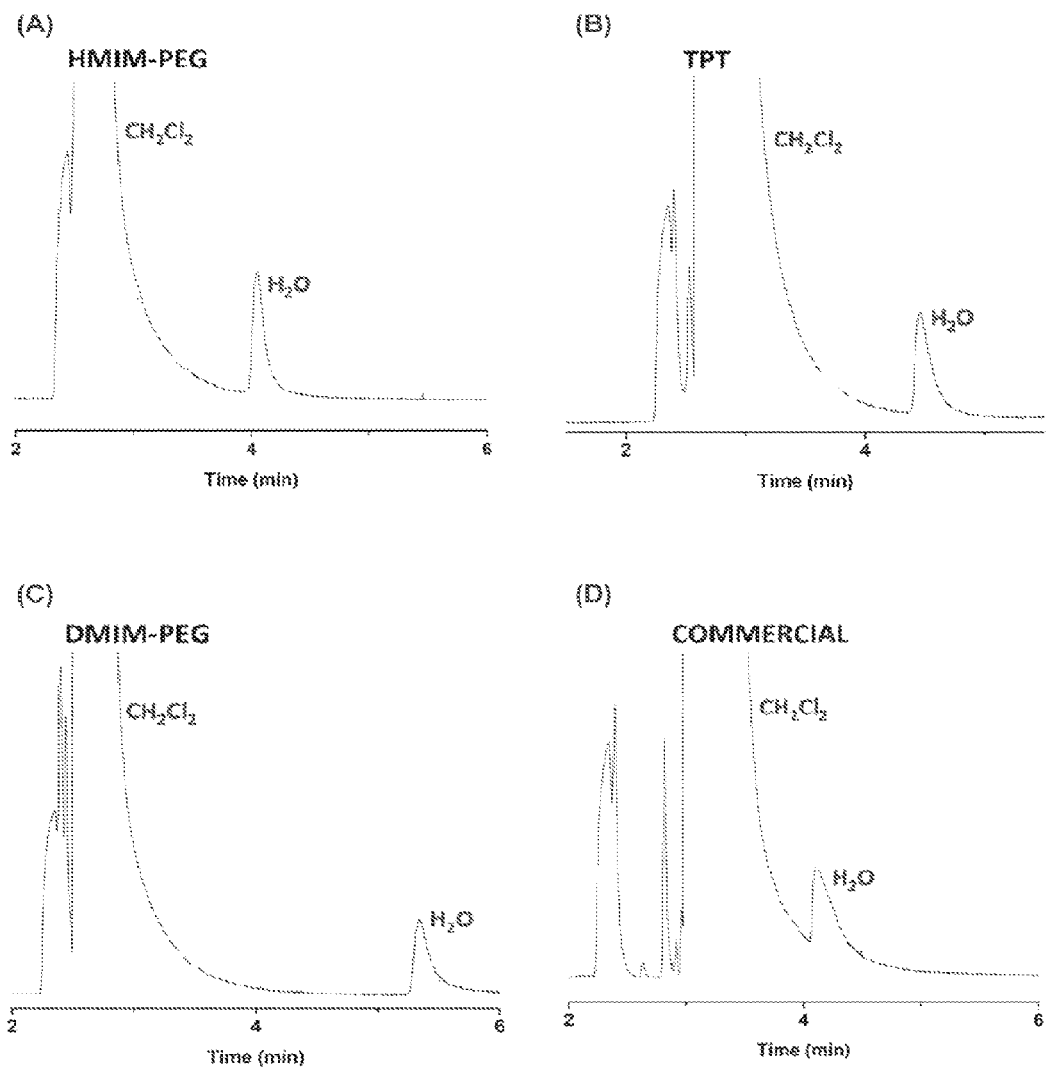
FIG. 3 is an example of improved resolution and peak symmetry using one of ionic liquid based stationary phase (A), (B) and (C), and a commercial PEG column (D).
Figure 4:
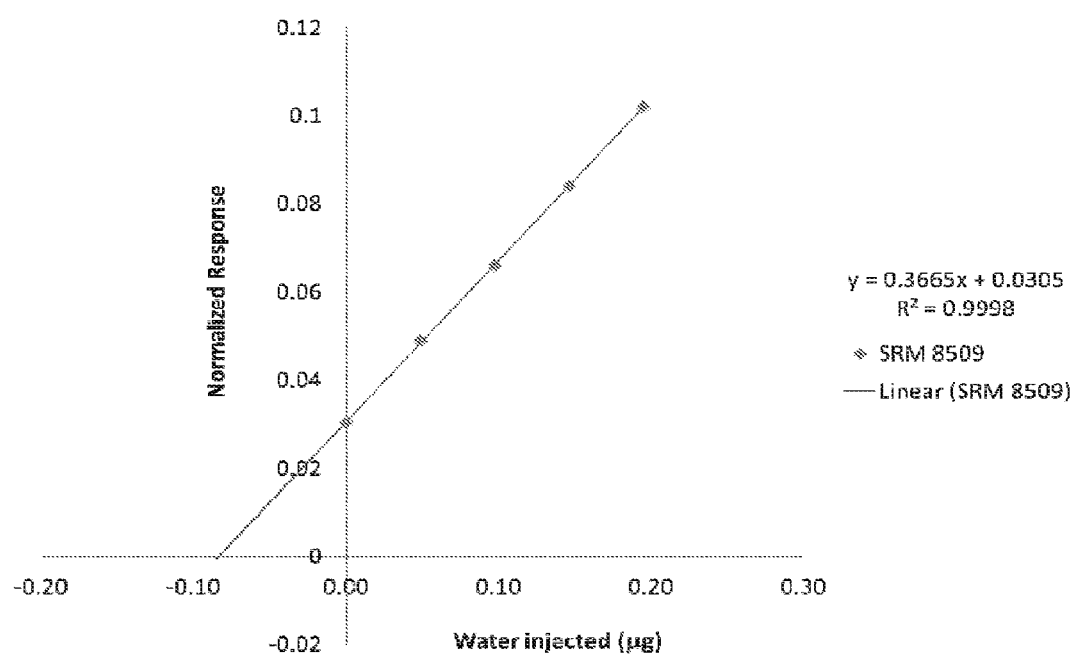
FIG. 4 is a plot of normalized response versus amount of spiked water injected onto HAIM-PEF column (50-200 nL volumes of water were spiked into 1 ml of SRM 8509 using 0.5 μl calibrated Hamilton syringe).

A comparison of the separation of water from methylene chloride on an IL column versus a commercial PEG type column is shown in FIG. 3 where the conditions were injection 1 µl, temperature 80° C. The ionic liquid based columns (A), (B) and (C) produced better peak shapes and selectivity even though the separation conditions were optimized for the PEG column and not the IL one. In all cases (for all solvent samples), the IL-based separations were substantially better in terms of selectivity and efficiency.

Table 3 compares the amount of water measured in ten solvents and a NIST methanol standard using four different capillary GC methods and the Karl Fischer titration (KFT). The samples were chosen so that the KFT analysis could be done without the use of special reagents (e.g., as are needed to quantify water in aldehydes and ketones). Also most of these samples could be analyzed on the commercial PEG column.

TABLE 3

Comparison of the ionic liquid GC results with the best results from the Karl Fischer Titration (KFT) and the use of a commercial PEG GC column.

| Sample | HMIM-PEG | | TTP | | DMIM-PEG | | Commercial | | KF[a] | |
|---|---|---|---|---|---|---|---|---|---|---|
| | H$_2$O/ppm | RSD[b] | H$_2$O/ppm | RSD[b] | H$_2$O/ppm | RSD[b] | H$_2$O/ppm | RSD[b] | H$_2$O/ppm | RSD[b] |
| Tetrahydrofuran | 110 | 6.0 | 108 | 5.8 | 117 | 8.1 | 77 | 12.0 | 179 | 5.2 |
| Dimethylformamide | 594 | 4.0 | 606 | 4.9 | 614 | 6.2 | X[c] | X[c] | 678 | 4.3 |
| t-Butyl alcohol | 2130 | 1.9 | 2010 | 6.2 | 1950 | 4.0 | 1868 | 8.3 | 2006 | 6.4 |
| Dimethyl sulfoxide | 773 | 2.9 | 800 | 4.4 | 820 | 5.0 | 740 | 11.3 | 796 | 4.6 |
| Ethanol | 890 | 2.0 | 880 | 3.8 | 880 | 2.0 | 670 | 11.2 | 809 | 4.0 |
| Ethyl acetate | 370 | 2.8 | 365 | 3.9 | 371 | 1.0 | 327 | 6.7 | 509 | 5.6 |
| Methanol | 209 | 7.1 | 198 | 4.6 | 203 | 5.0 | 173 | 21.0 | 241 | 6.0 |
| Methylene chloride | 48 | 8.2 | 52 | 6.3 | 47 | 7.3 | 78 | 5.5 | 117 | 3.3 |
| 1-Propanol | 308 | 4.0 | X[c] | X[c] | 285 | 3.2 | X[c] | X[c] | 365 | 7.1 |
| 2-Propanol | 180 | 3.9 | 171 | 2.4 | 162 | 3.0 | 179 | 14.0 | 232 | 4.0 |
| NIST MeOH Std. (97 ± 13 ppm) | 104 | 4.0 | 99 | 3.8 | 114 | 5.8 | 47 | 8.0 | 158 | 8.6 |

[a]Five grams of sample were used for all KFT except for those with the lowest water concentrations. Ten grams of sample were used for the methanol and tetrahydrofuran and fifteen grams for methylene chloride. Twelve grams of sample were used for the NIST methanol standard.
[b]Minimum of three determinations were done.
[c]No adequate value could be obtained with this column because of excess overlap between solvent and internal standard or between the solvent and the water peaks.

As can be seen from the data above, the ionic liquid based columns usually produced the most precise and accurate results (as indicated from the residual standard deviations (RSDs) and NIST standard respectively,). There are a few things to be noted about the data. First, no more than one microliter of sample was used for any of the capillary GC determinations. Conversely, the KF titrations utilized between 5 and 15 grams of sample depending on the water content of the solvents (larger samples were required for samples containing the least water) as shown in Table 3. The limits of detection (LOD) and limits of quantitation for the IL columns were better than those found for the commercial PEG column even when analyzing samples and using conditions that are necessary for favorable separations on the PEG column as shown in Table 3. The detection limit of coulometric KFT is 10 μg, and it requires at least 5 g of sample. The IL based GC method required only 0.2 μl of sample to obtain a much lower detection limit (about 2.0 ng or about 5,000×greater sensitivity) as shown in Table 4.

TABLE 4

Limits of detection (LOD) and limits of quantitation (LOQ) of water in the evaluated columns.

| | HMIM-PEG | | TTP | | DMIM-PEG | |
|---|---|---|---|---|---|---|
| Solvent | LOD/ng | LOQ/ng | LOD/ng | LOQ/ng | LOD/ng | LOQ/ng |
| MeOH/A[a] | 3.6 | 10.9 | 4.0 | 12.0 | 4.1 | 12.4 |
| THF/C[b] | 2.1 | 6.3 | 5.6 | 16.9 | 3.0 | 9.0 |

[a] "A" indicates that acetone was used as the internal standard.
[b] "C" indicates that acetonitrile was used as the internal standard.

Figure 5:
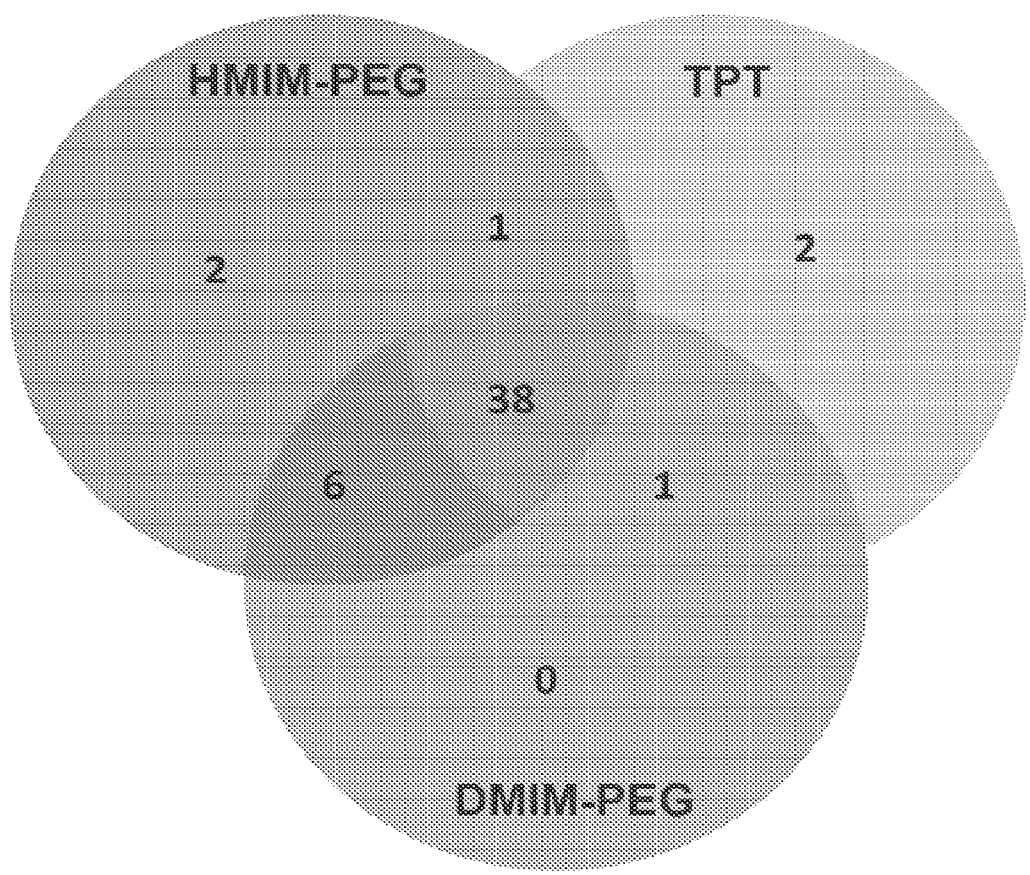
FIG. 5 is an illustration showing the number of successful water separations on each of the three IL based columns.

Table 5 lists the water content of 50 different solvents as determined with the three IL columns evaluated in this study. FIG. 5 indicates the number of these solvents that could be successfully analyzed on each column. Only two could only be done on each of the HMIM-PEG and TTP columns. The HMIM-PEG was the most broadly useful stationary phase as it produced adequate separations of water from 47 out of the 50 tested solvents. To be considered a successful separation, the water (analyte) peak had to be separated from both the solvent and at least one of the internal standards (i.e., acetone or acetonitrile). FIG. 5 shows that all three IL columns could be used to quantify water in 38 out of the 50 solvents. The HMIM-PEG-TFO overall was the most successful as it could be used to quantify water in 47 of the solvent samples, including two samples that were not amenable to separation on the other tested columns.

TABLE 5

Detection of water in 50 solvents.

| | HMIM-PEG | | TTP | | DMIM-PEG | |
|---|---|---|---|---|---|---|
| Sample | Water (ppm) | RSD % | Water (ppm) | RSD % | Water (ppm) | RSD % |
| Acetic acid | 420 | 1.0 | 410 | 5.9 | 440 | 5.0 |
| Acetone | 2380 | 3.8 | 2380 | 6.1 | 2520 | 0.3 |
| Acetonitrile | 103 | 3.0 | 98 | 6.9 | 103 | 2.7 |
| Anisole | X | X | 990 | 2.6 | 990 | 3.5 |
| Benzene | 18 | 2.4 | 17 | 8.4 | 21 | 9.5 |
| 1-Butanol | 1190 | 3.6 | 1150 | 5.8 | X | X |
| 2-Butanol | 3530 | 2.6 | X | X | 3380 | 2.3 |
| 2-Butanone | 730 | 3.7 | 760 | 1.2 | 710 | 5.8 |
| t-Butyl alcohol | 2130 | 1.9 | 2010 | 6.2 | 1950 | 4.0 |
| Carbon tetrachloride | 36 | 3.7 | 38 | 4.4 | 36 | 5.7 |
| Chlorobenzene | 38 | 9.6 | 42 | 8.9 | 39 | 3.1 |
| 1-Chlorobutane | 27 | 5.5 | 23 | 5.0 | 28 | 3.7 |
| Chloroform | 155 | 2.3 | 153 | 5.1 | 162 | 6.3 |
| 2-Chloropropane | 120 | 4.0 | 113 | 5.3 | 125 | 4.2 |
| Cyclohexane | 18 | 9.7 | 21 | 7 | 20 | 3.5 |
| Cyclohexanone | 8630 | 0.9 | 8450 | 5.4 | 8710 | 1.0 |
| 1,2-Dichlorobenzene | X | X | 12 | 6.0 | X | X |
| 1,2-Dichloroethane | 160 | 6.9 | 150 | 13.7 | 140 | 2.4 |
| 1,3-Dichloropropane | 114 | 4.9 | X | X | 102 | 1.5 |
| Diethyl ether | 400 | 7.6 | 420 | 1.6 | 390 | 6.4 |
| Di(ethylene glycol) ethyl ether | 950 | 4.3 | 970 | 9.5 | 930 | 2.1 |
| 1,2-Dimethoxy-ethane (glyme, DME) | 7500 | 1.5 | 7600 | 1.4 | 7300 | 0.6 |
| Dimethyl-formamide | 594 | 4.0 | 606 | 4.9 | 614 | 6.2 |
| Dimethyl sulfoxide | 773 | 2.9 | 800 | 4.4 | 820 | 5.0 |
| Dioxane | 3800 | 4.0 | 3700 | 3.5 | 3900 | 2.3 |
| Ethanol | 890 | 2.0 | 880 | 3.8 | 880 | 2.2 |
| Ethyl acetate | 370 | 2.8 | 365 | 3.9 | 370 | 1.4 |
| Ethylene glycol | 170000 | 3.5 | 169000 | 5.3 | 179000 | 3.2 |
| Heptane | 18 | 6.3 | 17 | 8.7 | 16 | 8.7 |
| Hexane | 14 | 5.3 | 17 | 9.5 | 16 | 9.0 |
| Methanol | 209 | 7.1 | 198 | 4.6 | 203 | 5.0 |
| Methyl t-butyl ether | 1900 | 1.1 | 1800 | 6.1 | 1900 | 6.6 |
| Methylene chloride | 48 | 8.2 | 52 | 6.3 | 47 | 7.3 |
| N-methyl-2-pyrrolidinone | 18700 | 5.7 | 18500 | 4.8 | 19000 | 2.1 |

TABLE 5-continued

Detection of water in 50 solvents.

| | HMIM-PEG | | TTP | | DMIM-PEG | |
|---|---|---|---|---|---|---|
| Sample | Water (ppm) | RSD % | Water (ppm) | RSD % | Water (ppm) | RSD % |
| Nitrobenzene | 119 | 2.5 | 109 | 8.5 | 117 | 3.9 |
| Nitromethane | 920 | 5.0 | X | X | X | X |
| Nitroethane | 770 | 3.2 | X | X | X | X |
| Octane | 13 | 8.0 | 17 | 10.0 | 14 | 5.1 |
| 1-Octanol | 190 | 4.6 | 210 | 7.0 | 190 | 5.6 |
| Pentane | 16 | 3.4 | 18 | 9.6 | 15 | 4.8 |
| Petroleum ether (ligroin) | 16 | 3.9 | 19 | 6.1 | 17 | 4.6 |
| 1-Propanol | 308 | 4.0 | X | X | 285 | 3.2 |
| 2-Propanol | 180 | 3.9 | 171 | 2.4 | 162 | 3.0 |
| Pyridine | X | X | 910 | 4.6 | X | X |
| Tetrahydrofuran | 110 | 6.0 | 108 | 5.8 | 117 | 8.1 |
| Toluene | 31 | 4.2 | 29 | 5.0 | 32 | 4.6 |
| Triethyl amine | 56 | 0.3 | 57 | 0.2 | 57 | 6.7 |
| o-Xylene | 74 | 7.7 | X | X | 76 | 4.9 |
| m-Xylene | 22 | 7.9 | X | X | 24 | 0.6 |
| p-Xylene | 23 | 9.2 | X | X | 26 | 0.2 |

The symbol "X" indicates that the water peak was not adequately separated from the solvent peak. All other experimental conditions are given in Tables 1 and 2.

The TTP TfO⁻ column was used to quantify water in 42 solvents, including pyridine and 1,2-dichlorobenzene which were not possible using the other two columns that were investigated. The DMIM-PEG $TfO_2^-$ column often gave the best, separation window between the water peak and solvent peaks, compared to the other columns. Hence all the separations that are possible on this column can be done at even higher temperatures that those used in this disclosure (Tables 3 and 4) or using temperature gradients (FIG. 2(B)) if desired. In most cases this means that many analyses times can be less than 3 minutes.

Figure 6:
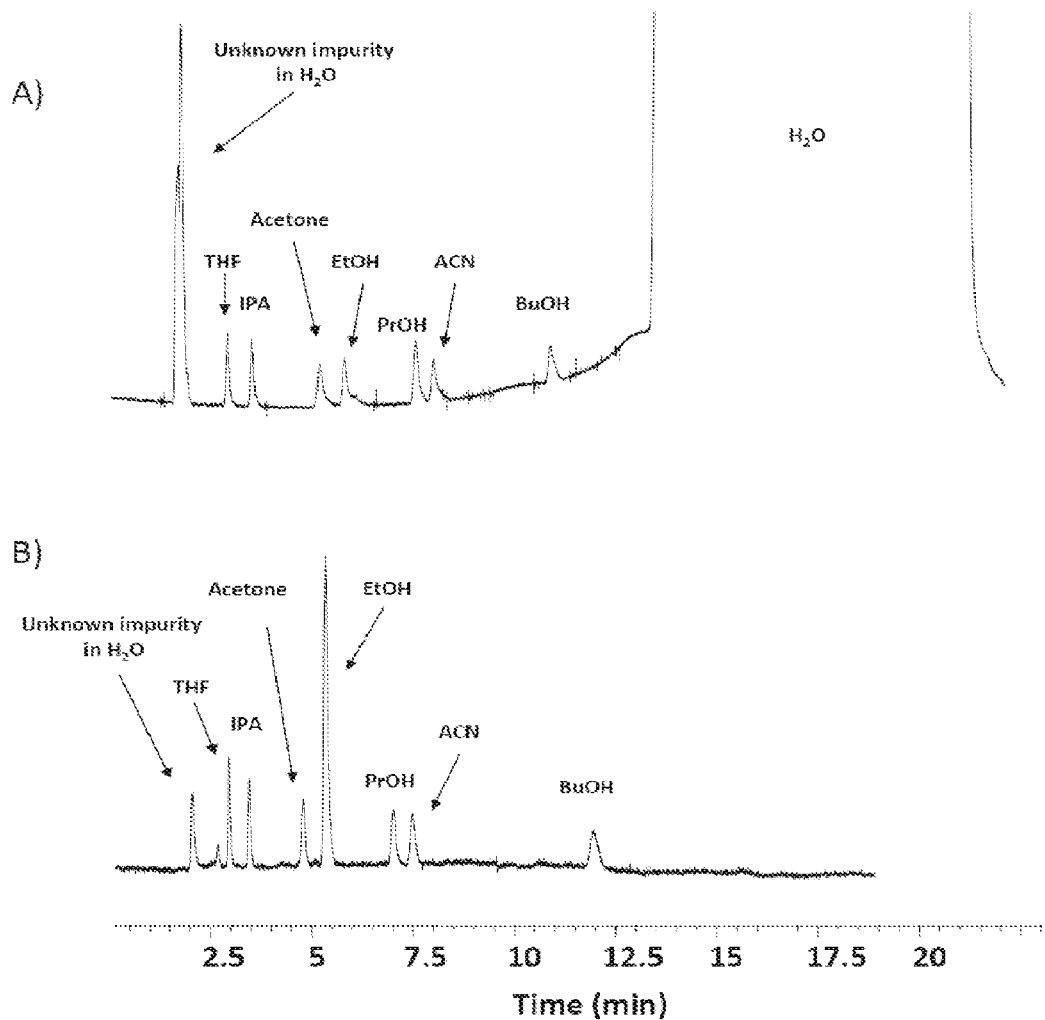
FIG. 6 is an example of the separation of organic solvents in water using ionic liquid based stationary phase.

FIG. 6 illustrates the use of capillary columns containing ionic liquid (IL) stationary phases in the measurement of trace amounts of organic solvents in water, wherein conditions for chromatogram A were DMIM-PEG, 40° C., 0.2 ml injection, thermal conductivity detector (all solvents: 100 mg/kg); and conditions for chromatogram B were DMIM-PEG, 40° C., 0.2 ml injection, flame ionization detector (all solvents: 5 mg/kg). In FIG. 6(A), TCD was used in order to show the elution of the water peak relative to trace organic solvents. In FIG. 6(B), even lower concentrations of the organic contaminants were seen when using flame ionization detection (FID). Water cannot be seen with this detector. The injection of water samples is not recommended on ordinary commercial columns that are not based on ionic liquids. Virtually all traditional commercial columns showed appreciable degradation and continuously changing chromatograms when analyzing water samples. Analyzing water for organic solvents tends to be much more damaging for these columns than analyzing organic solvents for trace amounts of water. For example, three successive commercial PEG columns had to be used for this study while the separations and conditions of all IL columns used remained unchanged throughout the study (>1,600 injections).

A rapid, facile IL-based GC method has been developed for the quantification of water in extremely diverse solvent samples. Limits of detection using this technique are superior when compared to KFT. Furthermore, the IL-GC methodology requires less sample and is free from other complications associated with KFT. The IL GC method can be used regardless of the chemical nature of the solvent and produces no additional waste products. When compared to other GC methods using commercially available PEG columns, the IL based columns possessed superior selectivity for water in all solvents tested. Further, they show no degradation or chromatographic changes with time. Typical analysis times ranged from <3 min to 7 min.

What is claimed is:

1. A method for detecting or quantitating water in a liquid sample comprising:
applying a liquid sample to a capillary column having a gas chromatography stationary phase comprising at least one tricationic species of Formula II:

$$Gc(A)_3 \qquad \text{Formula II}$$

and a counter-ion,
wherein Gc is phenyl, cycloalkyl, Si, C, N or P,
wherein each A is independently selected from the group consisting of:

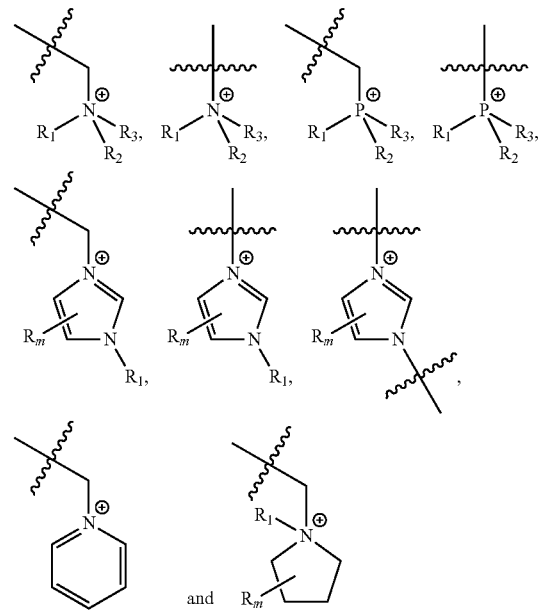

wherein each of $R_1$, $R_2$, $R_3$ and $R_m$ is independently selected from alkyl, alkoxy, carbocyclyl, carbocyclylalkyl, heterocyclyl, heterocyclylalkyl and hydroxyalkyl or $R_m$ can be H; and separating water from the liquid sample to detect or quantitate water in the liquid sample.

2. The method of claim 1, wherein the detecting or quantitating water comprises direct detection using a thermal conductivity detector.

3. The method of claim 1, further comprising producing a chromatogram showing one or more peaks of a molecule contained in the sample.

4. The method of claim 1, wherein the gas chromatography stationary phase is not substantially altered or degraded by a sample containing water.

5. The method of claim 1, wherein the capillary column comprises a solid support and a dicationic species adsorbed, absorbed or immobilized on the solid support.

6. The method of claim 1, wherein the method has a lower detection limit of about 2 ng water per 0.2 µL of sample.

7. The method of claim 1, wherein the counter-ion is selected from the group consisting of $F^-$, $NTf_2^-$, and triflate.

8. The method of claim 1, wherein the at least one tricationic species is selected from the group consisting of:

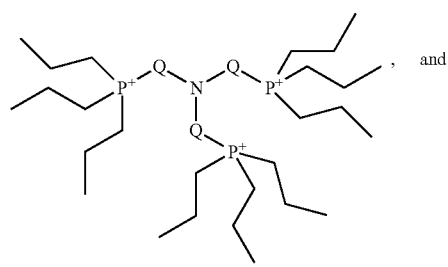

Formula II(a)

and

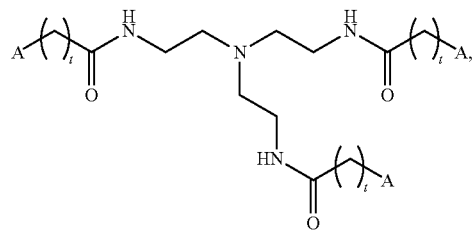

Formula II(b)

wherein each Q is independently $C_{1-10}$ alkylene, and each t is independently selected from the group consisting of 1 to 20, inclusive, each A is independently selected from the group consisting of:

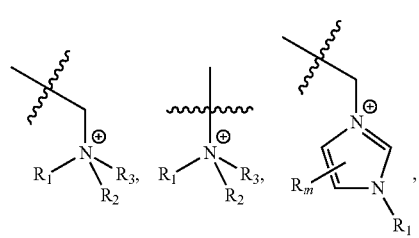

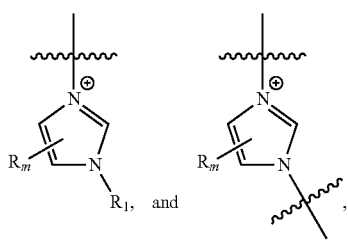

wherein each of $R_1$, $R_2$, $R_3$ and $R_m$ is independently selected from alkyl, alkoxy, carbocyclyl, carbocyclylalkyl, heterocyclyl, heterocyclylalkyl and hydroxyalkyl or $R_m$ can be H.

9. The method of claim 1, wherein the at least one tricationic species is selected from the group consisting of:

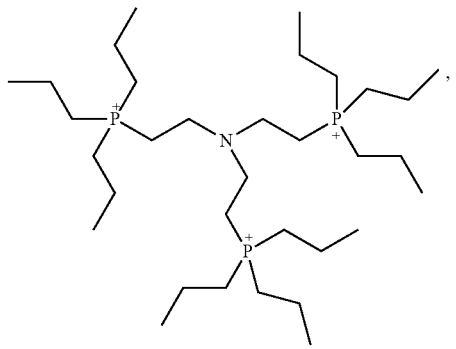

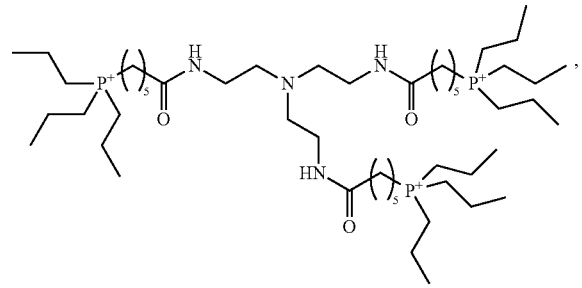

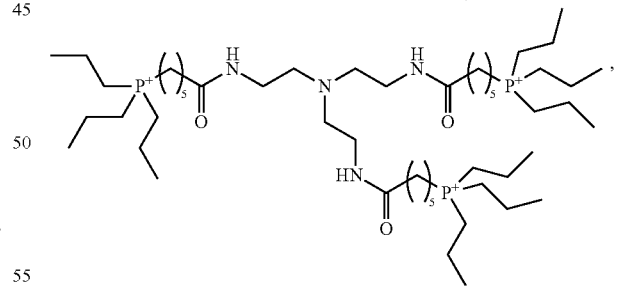

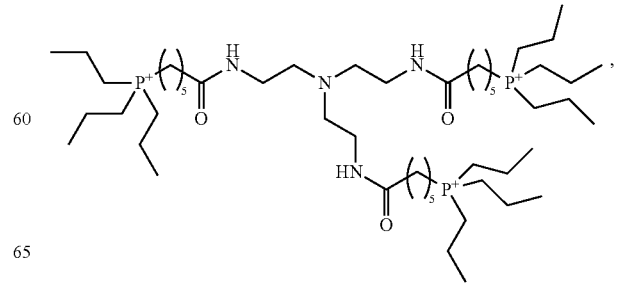

-continued

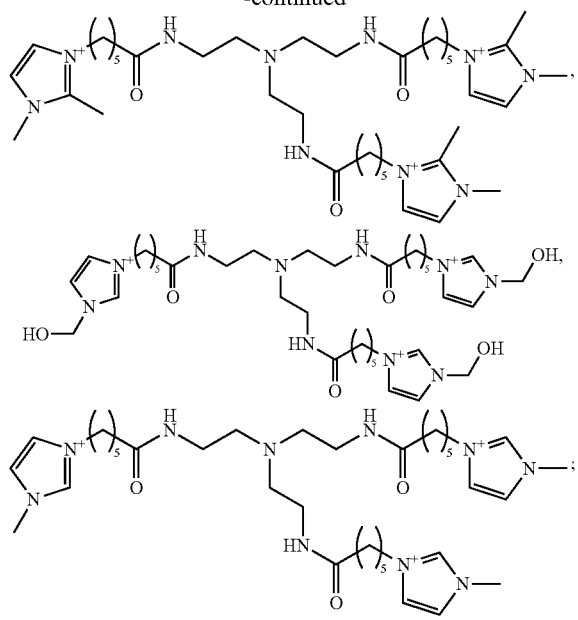

and
wherein the counter-ion is selected from F⁻, NTf₂⁻, and triflate.

10. The method of claim 1, wherein the at least one tricationic species and the counterion are:

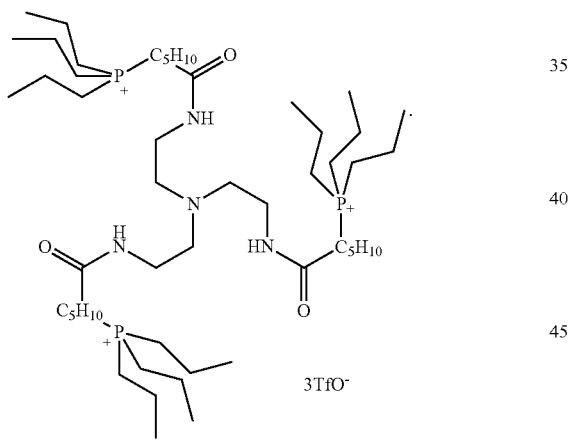

3TfO⁻

11. A gas chromatography method for detecting or quantitating a component in a liquid sample containing water, comprising:
applying a liquid sample to a capillary column having a gas chromatography stationary phase comprising a dicationic species of Formula I or a tricationic species of Formula II and a counter-ion:

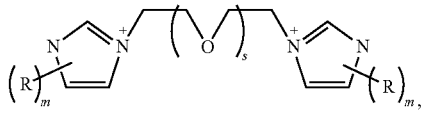

Formula I

Formula II

Gc(A)₃, wherein each R is independently selected from the group consisting of alkyl, alkoxy, carbocyclyl, carbocyclylalkyl, heterocyclyl, heterocyclylalkyl and hydroxyalkyl; each m is independently 0, 1, 2, 3 or 4; and s is 1, 2, 3, 4, 5 or 6, wherein Gc is phenyl, cycloalkyl, Si, C, N or P, wherein each A is independently selected from the group consisting of:

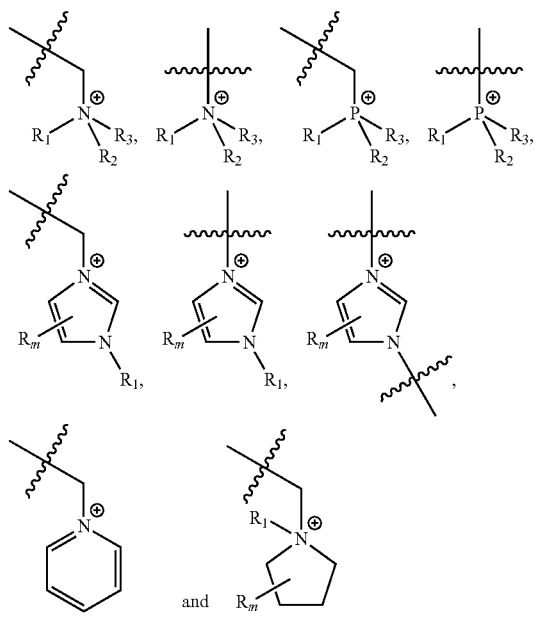

and wherein each of $R_1$, $R_2$, $R_3$ and $R_m$, is independently selected from alkyl, alkoxy, carbocyclyl, carbocyclylalkyl, heterocyclyl, heterocyclylalkyl and hydroxyalkyl or $R_m$, can be H;

separating a component from the liquid sample; and
quantitating the component by using a thermal conductivity detector.

12. The method of claim 11, wherein the sample is an organic solvent and the component is water.

13. The method of claim 11, wherein the sample is an aqueous solution and the component is organic.

* * * * *